(12) United States Patent
Zhang

(10) Patent No.: US 10,383,335 B2
(45) Date of Patent: Aug. 20, 2019

(54) BICYCLIC PYRAZOLE PESTICIDES

(71) Applicant: FMC Corporation, Philadelphia, PA (US)

(72) Inventor: Wenming Zhang, Newark, DE (US)

(73) Assignee: FMC Corporation, Philadelphia, PA (US)

(*) Notice: Subject to any disclaimer, the term of this patent is extended or adjusted under 35 U.S.C. 154(b) by 4 days.

(21) Appl. No.: 15/558,234

(22) PCT Filed: Mar. 29, 2016

(86) PCT No.: PCT/US2016/024662
§ 371 (c)(1),
(2) Date: Sep. 14, 2017

(87) PCT Pub. No.: WO2016/164200
PCT Pub. Date: Oct. 13, 2016

(65) Prior Publication Data
US 2018/0042236 A1 Feb. 15, 2018

Related U.S. Application Data

(60) Provisional application No. 62/144,972, filed on Apr. 9, 2015.

(51) Int. Cl.
*A01N 43/90* (2006.01)
*A01N 25/00* (2006.01)
*C07D 487/04* (2006.01)
*C07D 471/04* (2006.01)

(52) U.S. Cl.
CPC ............ *A01N 43/90* (2013.01); *A01N 25/00* (2013.01); *C07D 471/04* (2013.01); *C07D 487/04* (2013.01)

(58) Field of Classification Search
CPC ...... A01N 43/90; A01N 25/00; C07D 487/04; C07D 471/04
See application file for complete search history.

(56) References Cited

U.S. PATENT DOCUMENTS

| | | | |
|---|---|---|---|
| 7,795,262 | B2 | 9/2010 | Gao et al. |
| 9,504,251 | B2 | 11/2016 | Knueppel et al. |
| 9,688,681 | B2 | 6/2017 | Cerezo-Galvez et al. |
| 9,708,334 | B2 | 7/2017 | Basinger et al. |
| 9,802,961 | B2 | 10/2017 | Clark et al. |
| 9,832,999 | B1 | 12/2017 | Jeschke et al. |
| 9,920,059 | B2 | 3/2018 | Cerezo-Galvez et al. |
| 2017/0101422 | A1 | 4/2017 | Cerezo-Galvez et al. |
| 2017/0260183 | A1 | 9/2017 | Jeschke et al. |
| 2017/0260199 | A1 | 9/2017 | Hayashi et al. |
| 2017/0265474 | A1 | 9/2017 | Arlt et al. |
| 2017/0325459 | A1 | 11/2017 | Bretschneider et al. |
| 2017/0327487 | A1 | 11/2017 | Jeschke et al. |
| 2017/0355714 | A1 | 12/2017 | Cerezo-Galvez et al. |
| 2018/0037564 | A1 | 2/2018 | Zhang et al. |

FOREIGN PATENT DOCUMENTS

| | | | | |
|---|---|---|---|---|
| WO | 2013/106254 A1 | 7/2013 | | |
| WO | WO-2015038503 A1 * | 3/2015 | ........... | C07D 401/14 |
| WO | 2016/071499 A1 | 5/2016 | | |
| WO | 2016/087417 A1 | 6/2016 | | |
| WO | 2016/087422 A1 | 6/2016 | | |
| WO | 2016/144351 A1 | 9/2016 | | |
| WO | 2017/045955 A1 | 3/2017 | | |
| WO | 2017/062729 A1 | 4/2017 | | |
| WO | 2017/106000 A1 | 6/2017 | | |
| WO | 2018/011111 A1 | 1/2018 | | |
| WO | 2018/013482 A1 | 1/2018 | | |

\* cited by examiner

*Primary Examiner* — John Pak
*Assistant Examiner* — Andriae M Holt
(74) *Attorney, Agent, or Firm* — Sabine U. Epelbaum

(57) ABSTRACT

Disclosed are compounds of Formula 1, including all geometric and stereoisomers, N-oxides, and salts thereof,

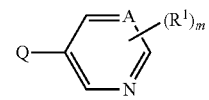

wherein
Q is

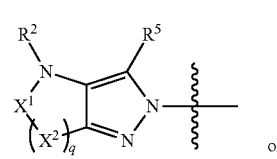

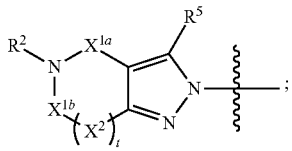

and A, $R^1$, m, $X^1$, $X^{1a}$, $X^{1b}$, $X^2$, $R^2$, $R^5$, q and t are as defined in the disclosure. Also disclosed are compositions containing the compounds of Formula 1 and methods for controlling an invertebrate pest comprising contacting the invertebrate pest or its environment with a biologically effective amount of a compound or a composition of the invention.

7 Claims, No Drawings

BICYCLIC PYRAZOLE PESTICIDES

FIELD OF THE INVENTION

This invention relates to certain substituted bicyclic azoles, their N-oxides, salts and compositions suitable for agronomic and nonagronomic uses, and methods of their use for controlling invertebrate pests such as arthropods in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes, but the need continues for new compounds that are more effective, less costly, less toxic, environmentally safer or have different sites of action.

SUMMARY OF THE INVENTION

This invention is directed to compounds of Formula 1 (including all geometric and stereoisomers), N-oxides, and salts thereof, and compositions containing them and their use for controlling invertebrate pests:

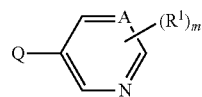

1 wherein
Q is

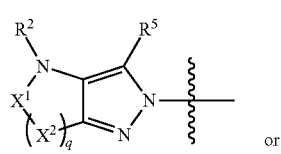
Q-1 or

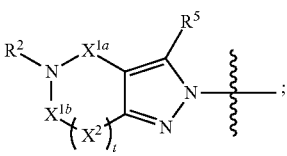
Q-2

A is CH, $CR^1$ or N;
$R^1$ is independently halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio;
m is 0, 1, 2 or 3;
$X^1$ is $C(R^{3a})(R^{3b})$, $S(O)_n$, $C(=O)$ or $C(=S)$;
$X^{1a}$ is $C(R^{3a})(R^{3b})$;
$X^{1b}$ is $C(R^{3a})(R^{3b})$, $S(O)_n$, $C(=O)$ or $C(=S)$;
each $X^2$ is independently $C(R^{3a})(R^{3b})$, O, $S(O)_n$, $C(=O)$ or $C(=S)$;

q is 1 or 2;
t is 0 or 1;
$R^2$ is $C(=Z)R^4$, $C(=Z)NR^6R^7$ or $LQ^a$; or $C_1$-$C_4$ alkyl substituted with $C(=Z)R^4$ or $C(=Z)NR^6R^7$, and optionally further substituted with up to 3 $R^y$;
each $R^{3a}$ and $R^{3b}$ is independently H, halogen, cyano or nitro; or $C_1$-$C_6$ alkyl, $C_2$-$C_6$ alkenyl or $C_2$-$C_6$ alkynyl, each unsubstituted or substituted with at least one $R^x$;
$R^4$ is H; or $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy, $C_1$-$C_6$ haloalkoxy or $C_3$-$C_6$ cycloalkoxy, each unsubstituted or substituted with at least one $R^x$; or $C(O)OR^{21}$, $C(O)NR^{15}R^{16}$ or $C(O)R^{22}$;
L is $C(=Z)$, $SO_2$ or a direct bond;
each Z is independently O, S or $NR^{10}$;
$R^5$ is H, halogen, cyano, nitro, $C_1$-$C_4$ alkyl, $C_3$-$C_6$ cycloalkyl, $C_1$-$C_4$ haloalkyl, $C_1$-$C_4$ alkoxy or $C_1$-$C_4$ haloalkoxy;
$R^6$ is H, $NR^{15}R^{16}$, $OR^{17}$, $C(=NR^{10})R^{11}$, $C(O)OR^{21}$, $C(O)NR^{15}R^{16}$, $C(O)R^{22}$, $S(O)_nR^{23}$ or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$;
$R^7$ is H or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$; or
$R^6$ and $R^7$ are taken together with the nitrogen atom to which they are attached to form a 3- to 10-membered ring containing ring members selected from carbon atoms and up to 2 heteroatoms independently selected from one oxygen atom, one sulfur atom, and up to 2 nitrogen atoms, wherein up to 2 carbon atom ring members are independently selected from $C(=O)$ and $C(=S)$ and the sulfur atom ring member is selected from S, S(O) or $S(O)_2$, said ring being unsubstituted or substituted with up to 4 $R^x$; or
$R^6$ and $R^7$ are taken together as $=S(O)_pR^{18}R^{19}$ or $=S(=NR^{20})R^{18}R^{19}$;
each $R^x$ is independently halogen, cyano, nitro, hydroxy, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_3$-$C_6$ cycloalkoxy, $C(=NR^{10})R^{11}$, $C(O)OR^{21}$, $C(O)NR^{15}R^{16}$, $OC(O)R^{22}$, $NR^{25}R^{26}$, $NR^{24}C(O)R^{22}$, $C(O)R^{22}$, $S(O)_nR^{23}$, $Si(R^{28})_3$, $OSi(R^{28})_3$ or $Q^a$;
each $R^y$ is independently halogen, cyano, hydroxy, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_3$-$C_6$ cycloalkoxy, $C(=NR^{10})R^{11}$, $C(O)OR^{21}$, $OC(O)R^{22}$, $NR^{25}R^{26}$, $NR^{24}C(O)R^{22}$, $C(O)R^{22}$ or $Q^a$;
each $R^{10}$ is independently $OR^{12}$, $S(O)_nR^{13}$ or $NHR^{14}$;
each $R^{11}$ is independently H; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$; or $C_1$-$C_6$ alkoxy, $C_1$-$C_6$ haloalkoxy, $C_3$-$C_6$ cycloalkoxy, $C(O)OR^{21}$, $C(O)NR^{15}R^{16}$, $C(O)R^{22}$;
each $R^{12}$ is independently $C_1$-$C_4$ alkyl, $C_3$-$C_6$ cycloalkyl, $C_1$-$C_4$ haloalkyl, $C(O)R^{22}$, $S(O)_nR^{13}$ or $Q^a$;
each $R^{13}$ is independently $C_1$-$C_4$ alkyl or $C_1$-$C_4$ haloalkyl;
$R^{14}$ is $C_1$-$C_4$ alkyl, $C_3$-$C_6$ cycloalkyl, $C_1$-$C_4$ haloalkyl, $C(O)R^{22}$ or $C(O)OR^{21}$; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;
$R^{15}$ is H, $NR^{15a}R^{16a}$, $OR^{17}$, $C(=NR^{10})R^{11}$, $C(O)OR^{21}$, $C(O)NR^{15a}R^{16a}$, $C(O)R^{22}$, $S(O)_nR^{23}$ or $Q^b$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$;

$R^{16}$ is H or $Q^b$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$; or $R^{15}$ and $R^{16}$ are taken together with the nitrogen atom to which they are attached to form a 3- to 10-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with up to 4 $R^x$; or $R^{15}$ and $R^{16}$ are taken together as $=S(O)_pR^{18}R^{19}$ or $=S(=NR^{20})R^{18}R^{19}$;

each $R^{15a}$ is independently H, $C_1$-$C_6$ alkyl, $C_1$-$C_4$ haloalkyl, C(O)$R^{27}$ or S(O)$_2R^{27}$; or phenyl or a 5- or 6-membered heterocyclic aromatic ring, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{16a}$ is independently H, $C_1$-$C_6$ alkyl or $C_1$-$C_4$ haloalkyl; or $R^{15a}$ and $R^{16a}$ are taken together with the nitrogen atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

$R^{17}$ is $C_1$-$C_4$ alkyl, $C_3$-$C_6$ cycloalkyl or $C_1$-$C_4$ haloalkyl; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{18}$ is independently $C_1$-$C_4$ alkyl or $C_1$-$C_4$ haloalkyl; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{19}$ is independently $C_1$-$C_4$ alkyl or $C_1$-$C_4$ haloalkyl; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or $R^{18}$ and $R^{19}$ are taken together with the sulfur atom to which they are attached to form a ring;

$R^{20}$ is H, cyano, $C_1$-$C_4$ alkyl, $C_1$-$C_4$ haloalkyl or C(O)$R^{22}$; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{21}$ is independently $C_1$-$C_4$ alkyl, $C_1$-$C_4$ haloalkyl, $C_3$-$C_6$ cycloalkyl or $C_3$-$C_6$ halocycloalkyl; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{22}$ is independently $C_1$-$C_4$ alkyl, $C_1$-$C_4$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_3$-$C_6$ cycloalkoxy or NR$^{25}$R$^{26}$; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{23}$ is independently $C_1$-$C_4$ alkyl, $C_1$-$C_4$ haloalkyl, $C_3$-$C_6$ cycloalkyl, $C_3$-$C_6$ halocycloalkyl, $C_3$-$C_6$ cycloalkylalkyl or $C_3$-$C_6$ halocycloalkylalkyl; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{24}$ is independently $C_1$-$C_4$ alkyl;

each $R^{25}$ is independently H, $C_1$-$C_4$ alkyl, $C_1$-$C_4$ haloalkyl, $C_1$-$C_4$ alkoxy or $C_1$-$C_4$ haloalkoxy; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{26}$ is independently $C_1$-$C_4$ alkyl or $C_1$-$C_4$ haloalkyl; or phenyl, unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or $R^{25}$ and $R^{26}$ are independently taken together with the nitrogen atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{27}$ is independently $C_1$-$C_6$ alkyl, $C_1$-$C_6$ haloalkyl, $C_1$-$C_6$ alkoxy, $C_1$-$C_6$ haloalkoxy or NR$^{29}$R$^{30}$; or phenyl or a 5- or 6-membered heterocyclic aromatic ring, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{28}$ is independently $C_1$-$C_6$ alkyl, $C_3$-$C_6$ cycloalkyl or phenyl;

each $R^{29}$ is independently H or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{30}$ is independently H or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or $R^{29}$ and $R^{30}$ are taken together with the nitrogen atom to which they are attached to form a 3- to 10-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with up to 4 substituents independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $Q^a$ is independently phenyl, a 5- or 6-membered heterocyclic aromatic ring or a 3- to 6-membered heterocyclic non-aromatic ring, each ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, each ring unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each n is independently 0, 1 or 2; and p is 1 or 2.

This invention also provides a composition comprising a compound of Formula 1, an N-oxide or a salt thereof, and at least one additional component selected from the group consisting of surfactants, solid diluents and liquid diluents. In one embodiment, this invention also provides a composition for controlling an invertebrate pest comprising a compound of Formula 1, an N-oxide or a salt thereof, and at least one additional component selected from the group consisting of surfactants, solid diluents and liquid diluents, said composition optionally further comprising at least one additional biologically active compound or agent.

This invention further provides a spray composition for controlling an invertebrate pest comprising a compound of Formula 1, an N-oxide or a salt thereof, or the compositions described above, and a propellant. This invention also provides a bait composition for controlling an invertebrate pest comprising a compound of Formula 1, an N-oxide or a salt thereof, or the compositions described in the embodiments above, one or more food materials, optionally an attractant, and optionally a humectant.

This invention further provides a trap device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

This invention provides a method for controlling an invertebrate pest comprising contacting the invertebrate pest or its environment with a biologically effective amount of a compound of Formula 1, an N-oxide or a salt thereof, (e.g., as a composition described herein). This invention also relates to such method wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent.

This invention also provides a method for protecting a seed from an invertebrate pest comprising contacting the seed with a biologically effective amount of a compound of Formula 1, an N-oxide or a salt thereof, (e.g., as a composition described herein). This invention also relates to the treated seed. This invention further provides a method for protecting an animal from an invertebrate parasitic pest comprising administering to the animal a parasitically effective amount of a compound of Formula 1, an N-oxide or a salt thereof, (e.g., as a composition described herein). This invention also provides for the use of a compound of Formula 1, an N-oxide or a salt thereof, (e.g., as a composition described herein) in protecting an animal from an invertebrate pest.

This invention also provides a method for increasing vigor of a crop plant comprising contacting the crop plant, the seed from which the crop plant is grown or the locus (e.g., growth medium) of the crop plant with a biologically effective amount of a compound of Formula 1 (e.g., as a composition described herein).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following:

A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods, nematodes and helminths of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes members of the phylum Nematoda, such as phytophagous nematodes and helminth nematodes parasitizing animals. The term "helminth" includes all of the parasitic worms, such as roundworms (phylum Nematoda), heartworms (phylum Nematoda, class Secernentea), flukes (phylum Platyhelminthes, class Tematoda), acanthocephalans (phylum Acanthocephala), and tapeworms (phylum Platyhelminthes, class Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of maize or corn, soybeans and other legumes, rice, cereal (e.g., wheat, oats, barley, rye and rice), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (e.g., berries and cherries) and other specialty crops (e.g., canola, sunflower and olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

The term "crop vigor" refers to rate of growth or biomass accumulation of a crop plant. An "increase in vigor" refers to an increase in growth or biomass accumulation in a crop plant relative to an untreated control crop plant. The term "crop yield" refers to the return on crop material, in terms of both quantity and quality, obtained after harvesting a crop plant. An "increase in crop yield" refers to an increase in crop yield relative to an untreated control crop plant.

The term "biologically effective amount" refers to the amount of a biologically active compound (e.g., a compound of Formula 1) sufficient to produce the desired biological effect when applied to (i.e. contacted with) an invertebrate pest to be controlled or its environment, or to a plant, the seed from which the plant is grown, or the locus of the plant (e.g., growth medium) to protect the plant from injury by the invertebrate pest or for other desired effect (e.g., increasing plant vigor).

The position of the variable $R^1$ in the structure of Formula 1 is described by the numbering system shown below.

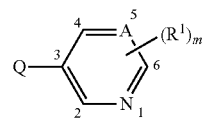

A wavy line in a structure fragment denotes the attachment point of the fragment to the remainder of the molecule. For example, when the variable Q in Formula 1 is defined as Q-1, the wavy line bisecting the bond in Q-1 means that Q-1 is attached to the remainder of the structure of Formula 1 at said position, as shown below.

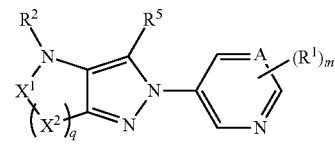

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Cycloalkyl" includes, for example, cyclopropyl, cyclobutyl, cyclopentyl and cyclohexyl.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C-$, $ClCH_2-$, $CF_3CH_2-$ and $CF_3CCl_2-$. The terms "halocycloalkyl", "haloalkoxy", "haloalkylthio", "haloalkenyl", "haloalkynyl", and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$.

The chemical abbreviations S(O) and S(=O) as used herein represent a sulfinyl moiety. The chemical abbreviations $SO_2$, $S(O)_2$ and $S(=O)_2$ as used herein represent a sulfonyl moiety. The chemical abbreviations C(O) and C(=O) as used herein represent a carbonyl moiety. The chemical abbreviations $CO_2$, C(O)O and C(=O)O as used herein represent an oxycarbonyl moiety. "CHO" means formyl.

The total number of carbon atoms in a substituent group is indicated by the "$C_i$-$C_j$" prefix where i and j are numbers from 1 to 6. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R^1)_m$, m is 0, 1, 2 or 3. Further, when the subscript indicates a range, e.g. $(R)_{i-j}$, then the number of substituents may be selected from the integers between i and j inclusive. When a group contains a substituent which can be hydrogen, for example $R^3$ or $R^4$, then when this substituent is taken as hydrogen, it is recognized that this is equivalent to said group being unsubstituted. When a variable group is shown to be optionally attached to a position, for example $(R^1)_m$ wherein m may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 (e.g., substituent $Q^a$) is carbocyclic or heterocyclic. The term "ring system" denotes two or more fused rings. The terms "bicyclic ring system" and "fused bicyclic ring system" denote a ring system consisting of two fused rings, which can be "ortho-fused", "bridged bicyclic" or "spirobicyclic". An "ortho-fused bicyclic ring system" denotes a ring system wherein the two constituent rings have two adjacent atoms in common. A "bridged bicyclic ring system" is formed by bonding a segment of one or more atoms to nonadjacent ring members of a ring. A "spirobicyclic ring system" is formed by bonding a segment of two or more atoms to the same ring member of a ring. The term "fused heterobicyclic ring system" denotes a fused bicyclic ring system in which at least one ring atom is not carbon. The term "ring member" refers to an atom or other moiety (e.g., C(=O), C(=S), S(O) or $S(O)_2$) forming the backbone of a ring or ring system.

The terms "carbocyclic ring", "carbocycle" or "carbocyclic ring system" denote a ring or ring system wherein the atoms forming the ring backbone are selected only from carbon. The terms "heterocyclic ring", "heterocycle" or "heterocyclic ring system" denote a ring or ring system in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a carbocyclic ring or heterocyclic ring can be a saturated or unsaturated ring. "Saturated" refers to a ring having a backbone consisting of atoms linked to one another by single bonds; unless otherwise specified, the remaining atom valences are occupied by hydrogen atoms. Unless otherwise stated, an "unsaturated ring" may be partially unsaturated or fully unsaturated. The expression "fully unsaturated ring" means a ring of atoms in which the bonds between atoms in the ring are single or double bonds according to valence bond theory and furthermore the bonds between atoms in the ring include as many double bonds as possible without double bonds being cumulative (i.e. no C=C=C or C=C=N). The term "partially unsaturated ring" denotes a ring comprising at least one ring member bonded to an adjacent ring member through a double bond and which conceptually potentially accommodates a number of non-cumulated double bonds between adjacent ring members (i.e. in its fully unsaturated counterpart form) greater than the number of double bonds present (i.e. in its partially unsaturated form).

Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and in which (4n+2) π electrons, where n is a positive integer, are associated with the ring to comply with Hückel's rule. The term "aromatic ring system" denotes a carbocyclic or heterocyclic ring system in which at least one ring of the ring system is aromatic. When a fully unsaturated carbocyclic ring satisfies Hückel's rule, then said ring is also called an "aromatic ring" or "aromatic carbocyclic ring". The term "aromatic carbocyclic ring system" denotes a carbocyclic ring system in which at least one ring of the ring system is aromatic. When a fully unsaturated heterocyclic ring satisfies Hückel's rule, then said ring is also called a "heteroaromatic ring", "aromatic heterocyclic ring" or "heterocyclic aromatic ring". The term "aromatic heterocyclic ring system" denotes a heterocyclic ring system in which at least one ring of the ring system is aromatic. The term "nonaromatic ring system" denotes a carbocyclic or heterocyclic ring system that may be fully saturated, as well as partially or fully unsaturated, provided that none of the rings in the ring system are aromatic. The term "nonaromatic carbocyclic ring system" denotes a carbocyclic ring in which no ring in the ring system is aromatic. The term "nonaromatic heterocyclic ring system" denotes a heterocyclic ring system in which no ring in the ring system is aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When a substituent is a 5- or 6-membered nitrogen-containing heterocyclic ring, it may be attached to the remainder of Formula 1 though any available carbon or nitrogen ring atom, unless otherwise described. As noted above, $Q^a$ can be (among others) phenyl optionally substituted with one or more substituents selected from a group of substituents as defined in the Summary of Invention. An example of phenyl optionally substituted with one to five substituents is the ring illustrated as U-1 in Exhibit 1, wherein $R^v$ is $R^x$ as defined in the Summary of the Invention for $Q^a$ and r is an integer from 0 to 5.

As noted above, $Q^a$ can be (among others) a 5- or 6-membered heterocyclic aromatic ring, optionally substituted with one or more substituents selected from a group of substituents as defined in the Summary of Invention. Examples of a 5- or 6-membered unsaturated aromatic heterocyclic ring optionally substituted with from one or more substituents include the rings U-2 through U-61 illustrated in Exhibit 1 wherein $R^v$ is any substituent as defined in the Summary of the Invention for $Q^a$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

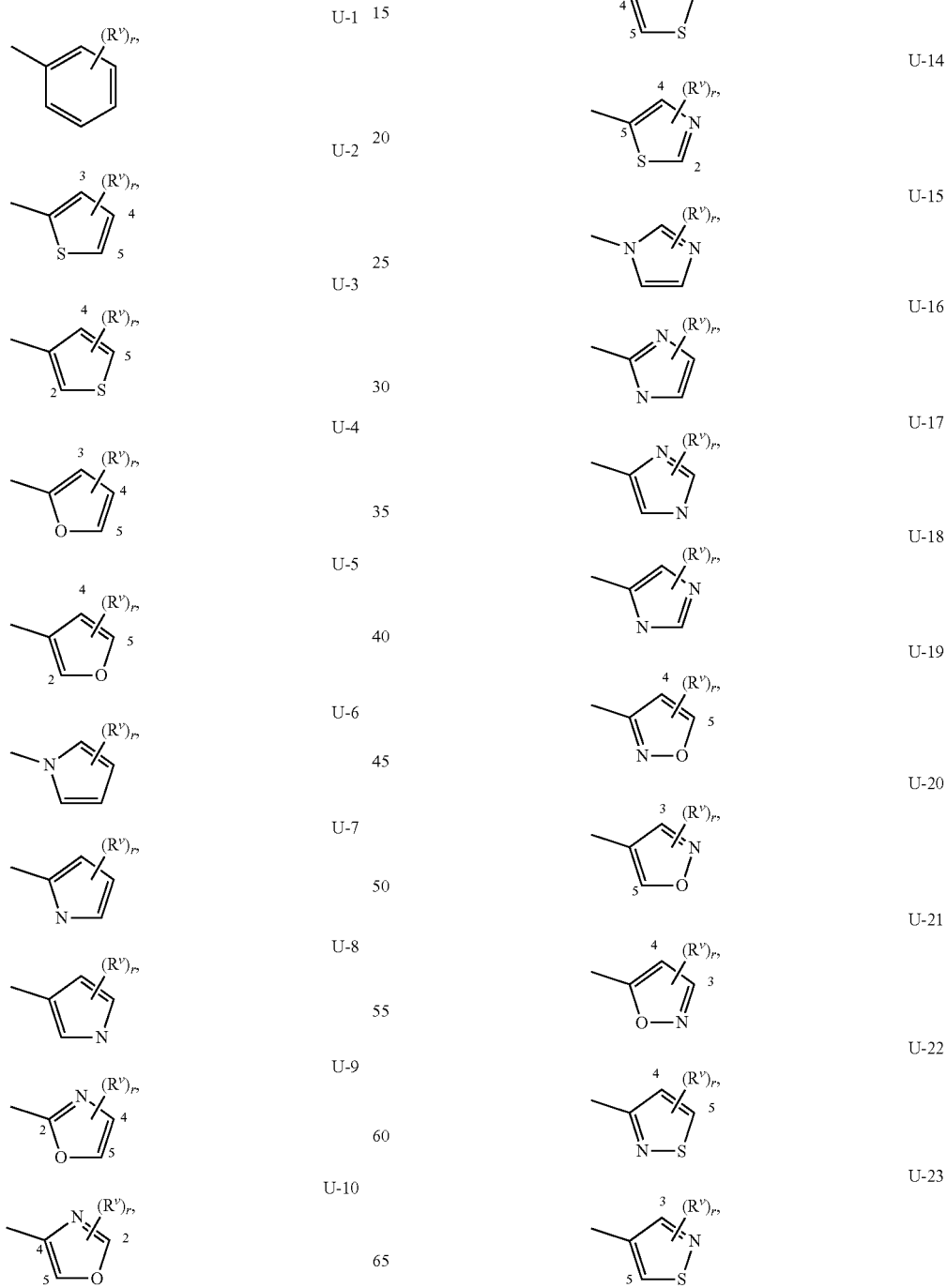

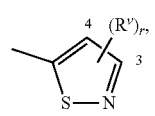 U-24
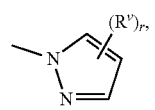 U-25
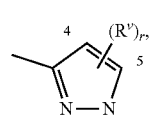 U-26
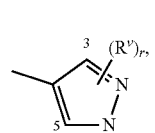 U-27
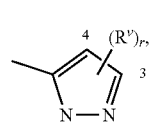 U-28
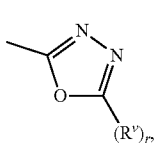 U-29
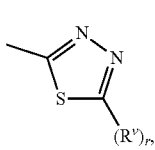 U-30
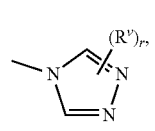 U-31
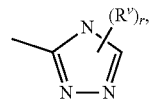 U-32
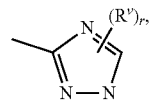 U-33
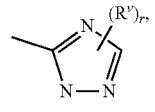 U-34
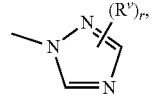 U-35
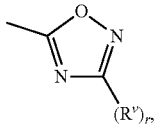 U-36
U-37
U-38
U-39
U-40
U-41
U-42
U-43
U-44
U-45
U-46
U-47
U-48

-continued

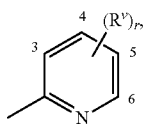 U-49

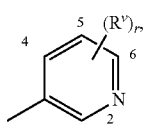 U-50

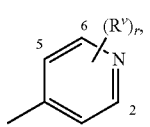 U-51

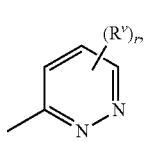 U-52

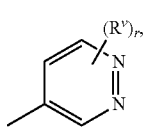 U-53

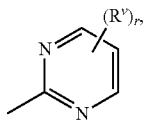 U-54

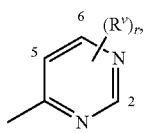 U-55

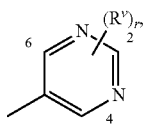 U-56

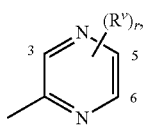 U-57

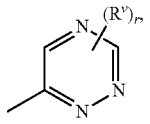 U-58

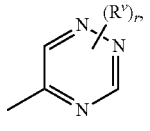 U-59

-continued

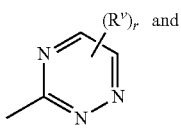 U-60

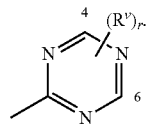 U-61

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. For a comprehensive discussion of all aspects of stereoisomerism, see Ernest L. Eliel and Samuel H. Wilen, *Stereochemistry of Organic Compounds*, John Wiley & Sons, 1994.

This invention comprises all stereoisomers, conformational isomers and mixtures thereof in all proportions as well as isotopic forms such as deuterated compounds.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of invertebrate pests. The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. Compounds of this invention may exist as one or more crystalline polymorphs. This invention comprises both individual polymorphs and mixtures of polymorphs, including mixtures enriched in one polymorph relative to others. For a comprehensive discussion of polymorphism see R. Hilfiker, Ed., *Polymorphism In the Pharmaceutical Industry*, Wiley-VCH, Weinheim, 2006.

Embodiments of the present invention as described in the Summary of the Invention include those described below. In the following Embodiments, reference to "a compound of Formula 1" includes the definitions of substituents specified in the Summary of the Invention unless further defined in the Embodiments.

Embodiment 1

A compound of Formula 1 wherein Q is Q-1.

Embodiment 2

A compound of Formula 1 wherein Q is Q-1 and $X^1$ is $C(R^{3a})(R^{3b})$.

Embodiment 3

A compound of Formula 1 wherein Q is Q-1, $X^1$ is $C(R^{3a})(R^{3b})$, and $X^2$ is $C(R^{3a})(R^{3b})$.

Embodiment 4

A compound of Formula 1 wherein Q is Q-1, $X^1$ is $C(R^{3a})(R^{3b})$, $X^2$ is $C(R^{3a})(R^{3b})$, and q is 2.

Embodiment 5

A compound of Formula 1 wherein Q is Q-1, $X^1$ is $CH_2$, $X^2$ is $CH_2$, and q is 2.

Embodiment 6

A compound of Formula 1 wherein Q is Q-2.

Embodiment 7

A compound of Formula 1 wherein Q is Q-2 and $X^{1b}$ is $C(R^{3a})(R^{3b})$.

Embodiment 8

A compound of Formula 1 wherein Q is Q-2, $X^{1b}$ is $C(R^{3a})(R^{3b})$, and $X^2$ is $C(R^{3a})(R^{3b})$.

Embodiment 9

A compound of Formula 1 wherein Q is Q-2, $X^{1b}$ is $C(R^{3a})(R^{3b})$, $X^2$ is $C(R^{3a})(R^{3b})$, and t is 1.

Embodiment 10

A compound of Formula 1 wherein Q is Q-2, $X^{1a}$ is $CH_2$, $X^{1b}$ is $CH_2$, $X^2$ is $CH_2$, and t is 1.

Embodiment 11

A compound of Formula 1 or any of Embodiments 1-10 wherein A is CH, $CR^1$ or N, and $R^1$ is halogen.

Embodiment 12

A compound of Formula 1 or Embodiment 11 wherein A is CH, CF or N.

Embodiment 12a

A compound of Embodiment 11 wherein A is CF or N.

Embodiment 13

A compound of Embodiment 11 wherein A is CH or CF.

Embodiment 14

A compound of Embodiment 11 wherein A is CH.

Embodiment 15

A compound of Embodiment 11 wherein A is N.

Embodiment 16

A compound of Formula 1 or any of Embodiments 1-10 wherein m is 1, and $R^1$ is $C_1$-$C_4$ alkyl, $C_1$-$C_4$ haloalkyl, $C_1$-$C_4$ alkoxy or halogen.

Embodiment 17

A compound of Embodiment 16 wherein $R^1$ is $CF_3$, OMe, Me, or F.

Embodiment 18

A compound of Embodiment 17 wherein $R^1$ is $CF_3$, OMe, Me, or F, and is in the 4-position.

Embodiment 19

A compound of Embodiment 18 wherein $R^1$ is $CF_3$, and is in the 4-position.

Embodiment 20

A compound of Formula 1 or any of Embodiments 1-10 wherein m is 0.

Embodiment 21

A compound of Formula 1 or any of Embodiments 1-20 wherein each $R^{3a}$ and $R^{3b}$ is H.

Embodiment 22

A compound of Formula 1 or any of Embodiments 1-21 wherein $R^2$ is C(=Z)$R^4$.

Embodiment 22a

A compound of Formula 1 or any of Embodiments 1-21 wherein $R^2$ is C(=O)$R^4$.

Embodiment 22b

A compound of Formula 1 or any of Embodiments 1-21 wherein $R^2$ is C(=O)$R^4$ and $R^4$ is $C_1$-$C_6$ alkyl substituted with S(O)$_n$$R^{23}$.

Embodiment 23

A compound of Formula 1 or any of Embodiments 1-21 wherein $R^2$ is C(=Z)NR$^6$R$^7$.

Embodiment 23a

A compound of Formula 1 or any of Embodiments 1-21 wherein $R^2$ is C(=O)NR$^6$R$^7$.

Embodiment 23b

A compound of Formula 1 or any of Embodiments 1-21 wherein $R^2$ is C(=O)$R^4$ or C(=O)NR$^6$R$^7$.

Embodiment 24

A compound of Formula 1 or any of Embodiments 1-21 wherein $R^2$ is LQ$^a$.

Embodiment 24a

A compound of Formula 1 or any of Embodiments 1-21 wherein $R^2$ is LQ$^a$ and L is direct bond.

Embodiment 24b

A compound of Formula 1 or any of Embodiments 1-21 wherein $R^2$ is LQ$^a$, L is direct bond, and Q$^a$ is a 6-membered heteroaromatic ring.

Embodiment 24c

A compound of Formula 1 or any of Embodiments 1-21 wherein $R^2$ is LQ$^a$, L is direct bond, and Q$^a$ is a 6-membered heteroaromatic ring having a nitrogen atom at the 2-position.

Embodiments of this invention, including Embodiments 1-24c above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-24c above as well as any other embodiments described herein, and any combination thereof, pertain to the compositions and methods of the present invention.

Combinations of Embodiments 1-24c are illustrated by:

Embodiment A

A compound of Formula 1 wherein
A is CH, CF and N; and
m is 0.

Embodiment B

A compound of Embodiment A wherein
Q is Q-1.

Embodiment C

A compound of Embodiment B wherein
$X^1$ is $CH_2$;
$X^2$ is $CH_2$; and
q is 2.

Embodiment D

A compound of Embodiment A wherein
Q is Q-2.

Embodiment E

A compound of Embodiment D wherein
$X^{1a}$ is $CH_2$;
$X^{1b}$ is $CH_2$;
$X^2$ is $CH_2$; and
t is 1.

Embodiment F

A compound of Embodiment C or Embodiment E wherein $R^2$ is $C(=O)R^4$ or $C(=O)NR^6R^7$.

Specific embodiments include compounds of Formula 1 selected from the group consisting of (compound numbers refer to Index Tables A-B):

2,4,6,7-tetrahydro-N-methyl-2-(3-pyridinyl)-N-(2,2-dimethoxyethyl)-5H-pyrazolo[4,3-c]pyridine-5-carboxamide (compound 14);

2,4,6,7-tetrahydro-2-(3-pyridinyl)-N-(2,2,2-trifluoromethyl)-5H-pyrazolo[4,3-c]pyridine-5-carboxamide (compound 15);

4,5,6,7-tetrahydro-2-(3-pyridinyl)-5-[2-(trifluoromethyl)-4-pyridinyl]-2H-pyrazolo[4,3-c]pyridine (compound 20);

1-[2,4,6,7-tetrahydro-2-(3-pyridinyl)-5H-pyrazolo[4,3-c]pyridin-5-yl]-3-[(2,2,2-trifluoroethyl)thio]-1-propanone (compound 22);

1-[2,4,6,7-tetrahydro-2-(3-pyridinyl)-5H-pyrazolo[4,3-c]pyridin-5-yl]-3-[(2,2,2-trifluoroethyl)sulfinyl]-1-propanone (compound 23);

2,4,6,7-tetrahydro-N-(3-methoxycyclobutyl)-2-(3-pyridinyl)-5H-pyrazolo[4,3-c]pyridine-5-carboxamide (compound 47);

4,5,6,7-tetrahydro-2-(3-pyridinyl)-5-(2-pyrazinyl)-2H-pyrazolo[4,3-c]pyridine (compound 48);

2-oxo-2-[2,4,6,7-tetrahydro-2-(3-pyridinyl)-5H-pyrazolo[4,3-c]pyridin-5-yl]ethyl N,N-dimethylcarbamate (compound 51); and 2,4,6,7-tetrahydro-β-oxo-2-(3-pyridinyl)-5H-pyrazolo[4,3-c]pyridine-5-propanenitrile (compound 54).

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent. Embodiments of the invention further include methods for controlling an invertebrate pest comprising contacting the invertebrate pest or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a biologically effective amount of a compound of any of the preceding Embodiments and a propellant. Embodiments of the invention further include a bait composition for controlling an invertebrate pest comprising a biologically effective amount of a compound of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include methods for protecting a seed from an invertebrate pest comprising contacting the seed with a biologically effective amount of a compound of any of the preceding Embodiments.

Embodiments of the invention also include methods for protecting an animal from an invertebrate parasitic pest comprising administering to the animal a parasitically effective amount of a compound of any of the preceding Embodiments.

Embodiments of the invention also include methods for controlling an invertebrate pest comprising contacting the invertebrate pest or its environment with a biologically effective amount of a compound of Formula 1, an N-oxide or a salt thereof, (e.g., as a composition described herein), provided that the methods are not methods of medical treatment of a human or animal body by therapy.

This invention also relates to such methods wherein the invertebrate pest or its environment is contacted with a composition comprising a biologically effective amount of a compound of Formula 1, an N-oxide or a salt thereof, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

The compounds of Formula 1 can be prepared by one or more of the following methods and variations as described in Schemes 1-3. The definitions of substituents in the compounds of Formulae 1-8 below are as defined above in the Summary of the Invention unless otherwise noted. Compounds of Formulae 1a-1f are various subsets of the compounds of Formula 1, and all substituents for Formulae 1a-1f are as defined above for Formula 1. The following abbreviations are used: THF is tetrahydrofuran, DMF is N,N-dimethylformamide, NMP is N-methylpyrrolidinone, Ac is acetate, MS is mesylate, Tf is triflate, and Nf is nonaflate.

Compounds of Formulae 1c and 1d can be prepared by the coupling of compounds of Formulae 1a or 1b with an appropriate acid of Formula 2 or acid chloride of Formula 3 as shown in Scheme 1. For a review of these coupling methods, see *Chemical Society Reviews* 2009, 38(2), pages 606-631.

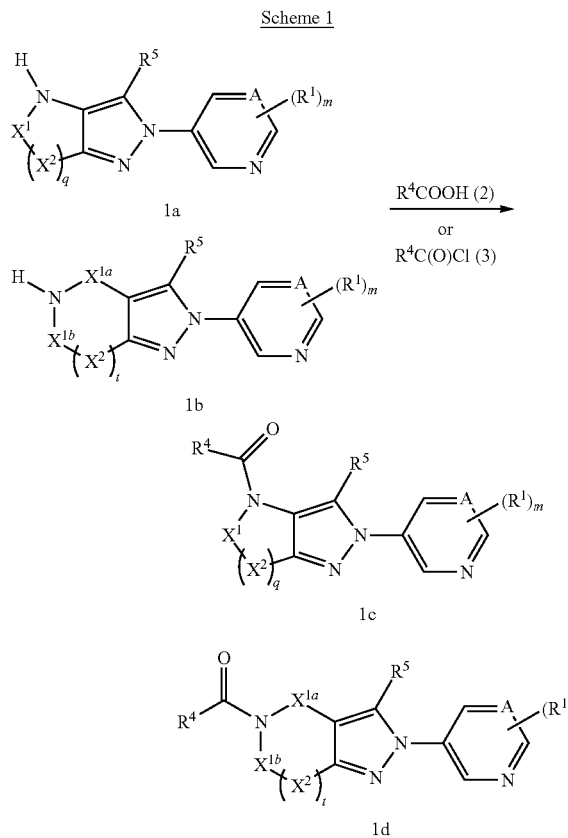

Compounds of Formulae 1e and 1f can be prepared by reaction of compounds of Formulae 1a or 1b with an appropriate carbamyl chloride of Formula 4 or isocyanate of Formula 5 as shown in Scheme 2 (for example, see *J. Heterocyclic Chem.* 2006, 43(3), pages 599-606).

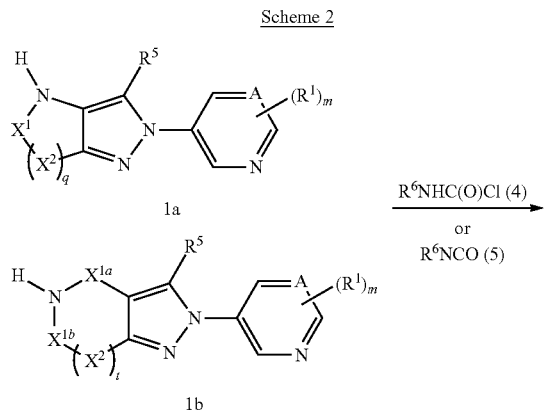

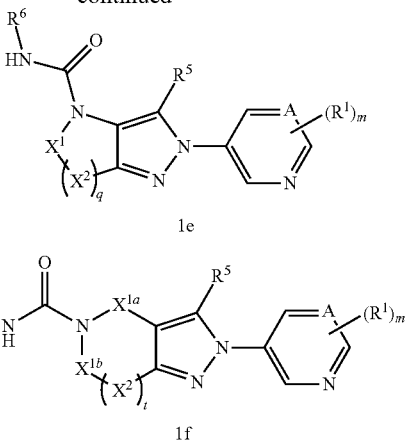

Compounds of Formula 1 can also be prepared by the method shown below in Scheme 3. In this method, the pyridine or pyrimidine of Formula 8 is treated with a compound of Formula 6 or 7 under metal-mediated coupling conditions to provide compounds of Formula 1. For a representative rhodium-catalyzed method, see *Organic Letters* 2013, 15(6), pages 1290-1293; for representative copper-catalyzed methods, see *Applied Catalysis, A: General* 2011, 403(1-2), pages 104-111; and *Journal of Molecular Catalysis A: Chemical* 2006, 256(1-2), pages 256-260.

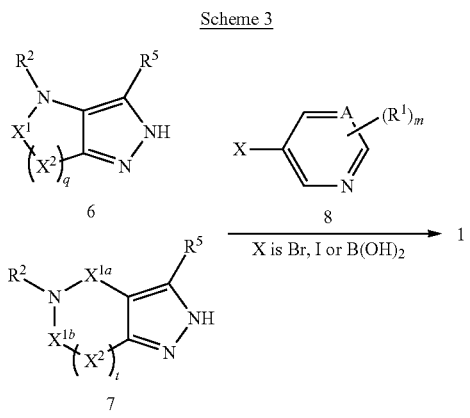

Compounds of Formula 1, and intermediates used in the preparation of compounds of Formula 1, wherein Z is S can be prepared by thionation of the corresponding compounds wherein Z is O with, for example, Lawesson's reagent (CAS No. 19172-47-5), Belleau's reagent (CAS No. 88816-02-8) or $P_2S_5$. The thionation reactions are typically conducted in solvents such as toluene, xylenes or dioxane, and at elevated temperature from 80° C. to the boiling point of the solvent.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after introduction of the reagents depicted in the individual schemes, additional routine synthetic steps not described in detail may be needed to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing sub stituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet. DMF means N,N-dimethylformamide. Compound numbers refer to Index Tables A-B.

Synthesis Example 1

Preparation of 2,4,6,7-tetrahydro-2-(3-pyridinyl)-5H-pyrazolo[4,3-c]pyridine-5-carboxylic acid, 2-(methoxycarbonyl)hydrazide (compound 10)

Step A: Preparation of 3-[(dimethylamino)methylene]-4-oxo-1-piperidinecarboxylic acid 1,1-dimethylethyl ester A solution of 4-oxo-1-piperidinecarboxylic acid 1,1-dimethylethyl ester (25 g, 126 mmol) and DMF-DMA (50 mL, 377 mmol) in 1,4-dioxane (200 mL) was heated at 100° C. for 20 hours. Upon completion, the reaction mixture was concentrated under reduced pressure to yield the title compound, which was used without further purification.

Step B: Preparation of 2,4,6,7-tetrahydro-5H-pyrazolo[4,3-c]pyridine-5-carboxylic acid 1,1-dimethylethyl ester A solution of 3-[(dimethylamino)methylene]-4-oxo-1-piperidinecarboxylic acid 1,1-dimethylethyl ester (34 g, 134 mmol) in ethanol (300 mL) was treated with hydrazine monohydrate (33.4 g, 668 mmol). The reaction mixture was heated to 90° C. for 3 hours, cooled to room temperature, and concentrated under reduced pressure to remove the ethanol. The residue was extracted with EtOAc, and the organic phase was dried over sodium sulfate, filtered and concentrated under reduced pressure. The resulting residue was purified by chromatography on silica gel eluted with 50% EtOAc/petroleum ether to afford the title compound (16.8 g).

Step C: Preparation of 2,4,6,7-tetrahydro-2-(3-pyridinyl)-5H-pyrazolo[4,3-c]pyridine-5-carboxylic acid 1,1-dimethylethyl ester A solution of 2,4,6,7-tetrahydro-5H-pyrazolo[4,3-c]pyridine-5-carboxylic acid 1,1-dimethylethyl ester (16.8 g, 75 mmol), 3-iodopyridine (30.96 g, 151 mmol), trans-N,N-dimethylcyclohexane-1,2-diamine (3.88 g, 37.6 mmol), copper iodide (2.87 g, 15 mmol) and potassium carbonate (20.86 g, 151 mmol) in 1,4-dioxane (350 mL) was heated to 110° C. for 6 hours. Upon completion, the reaction mixture was diluted with EtOAc, filtered through a pad of Celite®, and then concentrated under reduced pressure. The residue was extracted with EtOAc, and the organic phase was dried over sodium sulfate, filtered and concentrated under reduced pressure. The resulting residue was purified by chromatography on silica gel eluted with 40% EtOAc/petroleum ether to afford the title compound (18.6 g).

Step D: Preparation of 4,5,6,7-tetrahydro-2-(3-pyridinyl)-2H-pyrazolo[4,3-c]pyridine HCl in dioxane (4M, 50 mL, 200 mmol) was added dropwise at 0° C. to a solution of 2,4,6,7-tetrahydro-2-(3-pyridinyl)-5H-pyrazolo[4,3-c]pyridine-5-carboxylic acid 1,1-dimethylethyl ester (10 g, 33 mmol) in dichloromethane (50 mL). The reaction mixture was then stirred at room temperature for 2 hours. Upon completion, the reaction mixture was concentrated under reduced pressure. The residue was washed 2-3 times with petroleum ether before drying under vacuum. The resulting material (2 g) was treated with 10% NaOH in water to neutralize hydrogen chloride, and then extracted into EtOAc. The organic phase was dried over sodium sulfate, filtered, and concentrated to yield the title compound (1.3 g).

Step D: Preparation of 2,4,6,7-tetrahydro-2-(3-pyridinyl)-5H-pyrazolo[4,3-c]pyridine-5-carboxylic acid, 2-(methoxycarbonyl)hydrazide A solution of 4,5,6,7-tetrahydro-2-(3-pyridinyl)-2H-pyrazolo[4,3-c]pyridine (0.15 g, 0.7 mmol), triphosgene (0.65 g, 2.2 mmol) in dichloromethane (5 mL) was treated with triethylamine (0.16 g, 1.5 mmol) at 0° C. The reaction mixture was then allowed to stir at room temperature for 1 hour. Upon completion, the solvent was removed under a stream of nitrogen gas. The residue was then added to a solution of methyl carbazate (0.087 g, 0.97 mmol) and triethylamine (0.45 mL, 2.9 mmol) in dichloromethane (5 mL) at 0° C. After completion of the addition, the reaction mixture was stirred at room temperature for 24 hours. The reaction mixture was then extracted with dichloromethane, and the organic phase was dried over sodium sulfate, filtered, and concentrated under reduced pressure. The resulting residue was purified by chromatography on silica gel eluted with 5% MeOH/dichloromethane to yield 60 mg of the title compound, a compound of this invention. MS (M+1)=317.4.

Specific compounds of Formula 1, prepared by the methods and variations as described in preceding Schemes 1-3 and Synthesis Example 1, are shown in the following Index Tables.

Abbreviations used in the Index Tables may include: Cmpd means Compound, t is tertiary, c is cyclo, Me is methyl, Et is ethyl, Pr is propyl, i-Pr is isopropyl, Bu is butyl, c-Pr is cyclopropyl, c-Pn is cyclopentyl, c-Hx is cyclohexyl, t-Bu is tertiary-butyl, Ph is phenyl, OMe is methoxy, SMe is methylthio, and SO₂Me means methylsulfonyl. A wavy line or "—" in a structure fragment denotes the attachment point of the fragment to the remainder of the molecule.

INDEX TABLE A

| Cmpd. No. | R | Melting Point |
|---|---|---|
| 1 | —C(O)CH₂CH₂S(O)CH₂CH₂CF₃ | 150.8-160 |
| 2 | —C(O)CH₂CH₂SCH₂CF₃ | 102.1-110.5 |
| 3 | —C(O)CH₂CH₂SCH₂CH₂CF₃ | 128.6-129.1 |
| 4 | —CO₂(t-Bu) | 110-116 |
| 5 | —C(O)CH₂CH₂SO₂CH₂CH₂CF₃ | 216.6-218.5 |
| 6 | —C(O)CH₂CH₂S(O)CH₂CF₃ | 152.7-155.2 |
| 7 | —C(O)CH₂CH₂SO₂CH₂CF₃ | 183.4-196 |

INDEX TABLE B

| Cmpd. No. | R | Melting Point | MS (M+1) |
|---|---|---|---|
| 8 | —C(O)NHNHCO₂(t-Bu) | 97.5-120.3 | |
| 9 | —C(O)NHCH₂(tetrahydro-2-furanyl) | | 328.4 |
| 10 | —C(O)NHNHCO₂Me | | 317.4 |
| 11 | —C(O)NHCH₂(2-pyrimidinyl) | 137-151.9 | |
| 12 | —C(O)NHCH₂(5-methyl-2-pyrazinyl) | 156.6-173.7 | |
| 13 | —C(O)NHCH₂(2,2-difluorocyclopropyl) | 124.8-132.9 | |
| 14 | —C(O)N(Me)CH₂CF₃ | 136-138.4 | |
| 15 | —C(O)NHCH₂CH(OMe)₂ | | 332.2 |
| 16 | —C(O)NHCH₂CH(OEt)₂ | | 360.2 |
| 17 | —C(O)N(Me)(cyclopropyl) | 95.9-107.8 | |
| 18 | 6-(trifluoromethyl)pyridin-2-yl | | 346.2 |
| 19 | 5-(trifluoromethyl)pyridin-2-yl | 158.3-163.2 | |
| 20 | 2-(trifluoromethyl)pyridin-4-yl | | 346 |
| 21 | —CO₂(t-Bu) | | 301.2 |
| 22 | —C(O)CH₂CH₂SCH₂CF₃ | | 371 |
| 23 | —C(O)CH₂CH₂S(O)CH₂CF₃ | 137-142.9 | |
| 24 | —C(O)CH₂CH₂SO₂CH₂CF₃ | 138.2-149.9 | |
| 25 | —C(O)CH₂CH₂SO₂CH₂CH₂CF₃ | | 417.2 |
| 26 | —C(O)CH₂CH₂SCH₂CH₂CF₃ | | 385.2 |
| 27 | —C(O)CH₂CH₂S(O)CH₂CH₂CF₃ | | 401.2 |
| 28 | —C(O)NHCH₂CF₃ | 118.3-155.3 | |
| 29 | —C(O)NHMe | 212-224.2 | |
| 30 | —C(O)NMe₂ | 149.4-152.1 | |
| 31 | —C(O)NHEt | 151.1-170.5 | |
| 32 | —C(O)N(Me)Et | 102.5-111.9 | |
| 33 | —C(O)OMe | | 259.2 |
| 34 | —CH₂COOH | 246.2-268.4 | |
| 35 | —CH₂C(O)OMe | | 273.2 |
| 36 | —CH₂C(O)NHEt | | 286.2 |
| 37 | —CH₂C(O)NHCH(Me)CH₂OMe | | 330.2 |
| 38 | —CH₂C(O)NHCH₂CH(OMe)₂ | | 346.2 |
| 39 | —CH₂C(O)NH(n-Bu) | | 314.2 |
| 40 | —CH₂C(O)NHCH₂(tetrahydro-2-furanyl) | | 342.2 |
| 41 | —CH₂C(O)NHNHC(O)OMe | | 331.2 |
| 42 | —CH₂C(O)NHC(Me)₂CN | | 325.2 |
| 43 | —CH₂C(O)NHCH₂(2-pyrimidinyl) | | 350.4 |
| 44 | —CH₂C(O)NH(cyclopropyl) | 172-176.6 | |
| 45 | —C(O)N(Et)CH₂C≡CH | | 310 |
| 46 | —C(O)NHCH(Me)CH₂OMe | | 316.2 |
| 47 | —C(O)NH(3-methoxycyclobutyl) | 150.2-170.3 | |
| 48 | 2-pyrazinyl | 125.1-135.1 | |

INDEX TABLE B-continued

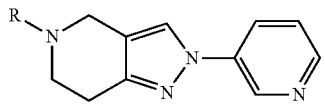

| Cmpd. No. | R | Melting Point | MS (M+1) |
|---|---|---|---|
| 49 | 2-pyridinyl | 117-125.1 | |
| 50 | —C(O)CH₂OH | 131.4-134.9 | |
| 51 | —C(O)CH₂OC(O)N(Me)₂ | 150-157.2 | |
| 52 | 3-pyridinyl | 107.4-117.7 | |
| 53 | —C(O)C(O)NHC(O)OMe | 128.8-144.9 | |
| 54 | —C(O)CH₂CN | 148.9-166.1 | |
| 55 | —C(O)C(O)NHC(O)NHMe | | 329.2 |
| 56 | —C(O)C(O)NHC(O)N(Me)₂ | 44.1-56.1 | |
| 57 | —C(O)CH₂Cl | 220.2-258.1 | |
| 58 | —CH₂C(O)NHC(O)NHMe | 162.5-178.2 | |

Examples of intermediates useful in the preparation of compounds of this invention are shown in Tables I-1 through I-8. The following abbreviations are used in the Tables which follow: Me means methyl, Et means ethyl, Ph means phenyl, C(O) means carbonyl and CHO means formyl.

TABLE I-1

| A |
|---|
| CH |
| CF |
| N |

TABLE I-2

| A |
|---|
| CH |
| CF |
| N |

TABLE I-3

| A |
|---|
| CH |
| CF |
| N |

TABLE I-4

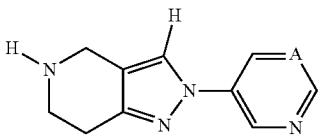

| A |
|---|
| CH |
| CF |
| N |

TABLE I-5

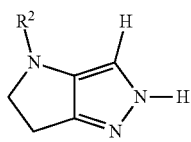

—C(O)Me
—C(O)Et
—C(O)Pr
—C(O)(i-Pr)
—C(O)CH$_2$(c-Pr)
—C(O)CH(Me)(c-Pr)
—C(O)Bu
—C(O)(s-Bu)
—C(O)(i-Bu)
—C(O)(t-Bu)
—C(O)CH$_2$Ph
—C(O)CH$_2$CH=CH$_2$
—C(O)CH$_2$C≡CH
—C(O)C(Me)$_2$C≡CH
—C(O)CH$_2$CH$_2$F
—C(O)CH$_2$CHF$_2$
—C(O)CH$_2$CF$_3$
—C(O)CH(Me)CF$_3$
—C(O)CH$_2$CH$_2$CF$_3$
—C(O)CH$_2$CF$_2$CF$_3$
—C(O)CH$_2$CF$_2$CH$_3$
—C(O)CH$_2$CH$_2$CF$_2$CF$_3$
—C(O)CH(i-Pr)CF$_3$
—C(O)CH$_2$CH$_2$OMe
—C(O)CH$_2$OEt
—C(O)CH$_2$CH$_2$O(i-Pr)
—C(O)CH$_2$CH$_2$OEt
—C(O)CH$_2$CH$_2$CH$_2$OMe
—C(O)CH$_2$CH(Me)OMe
—C(O)CH(Et)CH$_2$OMe
—C(O)CH(Me)CH$_2$OMe
—C(O)CH$_2$CH$_2$S(O)Me
—C(O)CH$_2$CH$_2$SMe
—C(O)CH$_2$CH$_2$SEt
—C(O)CH$_2$CH$_2$SO$_2$Me
—C(O)CH$_2$CH$_2$SO$_2$Et
—C(O)CH$_2$CH$_2$S(O)Et
—C(O)CH$_2$CH$_2$S(O)(t-Bu)
—C(O)CH$_2$CH$_2$S(t-Bu)
—C(O)CH(Me)CH$_2$SMe
—C(O)CH$_2$CH$_2$SO$_2$(t-Bu)
—C(O)CH(Me)CH$_2$SO$_2$Me
—C(O)CH(Me)CH$_2$S(O)Me
—C(O)CH$_2$CH$_2$S(O)CH$_2$CF$_3$
—C(O)CH$_2$CH$_2$SCH$_2$CF$_3$
—C(O)CH$_2$CH$_2$SO$_2$CH$_2$CF$_3$
—C(O)CH$_2$CH$_2$SO$_2$CH$_2$CH$_2$CF$_3$
—C(O)CH$_2$CH$_2$SCH$_2$CH$_2$CF$_3$
—C(O)CH$_2$CH$_2$S(O)CH$_2$CH$_2$CF$_3$
—C(O)CH$_2$CN
—C(O)CH$_2$CH$_2$CN
—C(O)C(Me)$_2$CN
—C(O)CH$_2$CH$_2$N(i-Pr)$_2$

TABLE I-5-continued

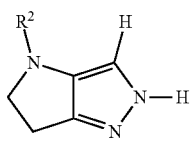

—C(O)CH$_2$CH$_2$N(Me)$_2$
—C(O)CH$_2$CH(OMe)$_2$
—C(O)(c-Pr)
—C(O)(c-Bu)
—C(O)(1-methylcyclopropyl)
—C(O)(3-methoxycyclobutyl)
—C(O)CH(Ph)(c-Pr)
—C(O)CH(Me)(c-Pr)
—C(O)(3-thietanyl)
—C(O)(3,3-difluorocyclobutyl)
—C(O)(3-oxetanyl)
—C(O)CH$_2$(oxiranyl)
—C(O)(3-thietanyl-1,1-dioxide)
—C(O)(3-thietanyl-1-oxide)
—C(O)CH$_2$(CH(—OC(Me)$_2$OCH$_2$—))
—C(O)CH$_2$(tetrahydro-2-furanyl)
—C(O)CH$_2$(2-furanyl)
—C(O)(tetrahydro-2-furanyl)
—C(O)CH$_2$(2-thienyl)
—C(O)CH$_2$(CH(—OCH$_2$CH$_2$O—)
—C(O)CH$_2$CO$_2$Me
—C(O)CH$_2$(2,2-difluorocyclopropyl)
—C(O)C(—CH$_2$CH$_2$—)CO$_2$Me
—C(O)CH(Me)CO$_2$Et
—C(O)CH(i-Pr)CO$_2$Me
—C(O)CH$_2$C(O)NHMe
—C(O)CH$_2$C(O)NMe$_2$
—C(O)CH(Me)C(O)NHMe
—C(O)CH(Me)C(O)NH(t-Bu)
—C(O)CH$_2$(6-CF$_3$-2-pyridinyl)
—C(O)CH(Me)C(O)NMe$_2$
—C(O)CH$_2$(3-CF$_3$-2-pyridinyl)
—C(O)CH$_2$(5-CF$_3$-2-pyrimidinyl)
—C(O)CH$_2$(4-CF$_3$-2-pyridinyl)
—C(O)CH$_2$(4-CF$_3$-2-pyrimidinyl)
—C(O)CH$_2$(6-methyl-2-pyridinyl)
—C(O)CH$_2$(5-CF$_3$-2-pyridinyl)
—C(O)CH$_2$(3-methyl-2-pyridinyl)
—C(O)CH$_2$(5-methyl-2-pyrimidinyl)
—C(O)CH$_2$(4-methyl-2-pyridinyl)
—C(O)CH$_2$(4-methyl-2-pyrimidinyl)
—C(O)CH$_2$(6-methoxy-2-pyridinyl)
—C(O)CH$_2$(5-methyl-2-pyridinyl)
—C(O)CH$_2$(3-methoxy-2-pyridinyl)
—C(O)CH$_2$(5-methoxy-2-pyrimidinyl)
—C(O)CH$_2$(4-methoxy-2-pyridinyl)
—C(O)CH$_2$(4-methoxy-2-pyrimidinyl)
—C(O)CH$_2$(5-pyrimidinyl)
—C(O)CH$_2$(5-methoxy-2-pyridinyl)
—C(O)CH$_2$(2-pyrimidinyl)
—C(O)CH$_2$(3-(OCF$_3$)phenyl)
—C(O)CH$_2$(6-bromo-2-pyridinyl)
—C(O)CH$_2$(5-methyl-2-pyrazinyl)
—C(O)CH$_2$(4-pyridinyl)
—C(O)CH$_2$(2-thiazolyl)
—C(O)Ph
—C(O)(3-pyridinyl)
—C(O)CH$_2$(2-pyridinyl)
—C(O)(2-pyridinyl)
—C(O)(2-pyrazinyl)
—C(O)CH$_2$(3-pyridinyl)
—C(O)(4-pyridinyl)
—C(O)(4-CF$_3$-2-pyridinyl)
—C(O)CH$_2$CH$_2$(2-pyridinyl)
—C(O)(3-CF$_3$-2-pyridinyl)
—C(O)(4-CF$_3$-2-pyrimidinyl)
—C(O)CH$_2$CH$_2$CH$_2$(2-pyridinyl)
—C(O)(5-CF$_3$-2-pyridinyl)
—C(O)(5-CF$_3$-2-pyrazinyl)
—C(O)(6-CF$_3$-2-pyridinyl)

TABLE I-5-continued

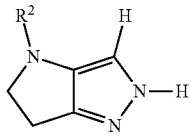

R[2]

—C(O)CH$_2$CH$_2$N(—C(O)CH$_2$CH$_2$C(O)—)
—C(O)CH$_2$CH$_2$CH$_2$(1-imidazolyl)
—C(O)(5-CF$_3$-2-pyrimidinyl)
—C(O)CH(—C(O)OCH$_2$CH$_2$—)
—C(O)NHMe
—C(O)NHEt
—C(O)NHPr
—C(O)NH(i-Pr)
—C(O)NHCH$_2$(c-Pr)
—C(O)NHCH(Me)(c-Pr)
—C(O)NHBu
—C(O)NH(s-Bu)
—C(O)NH(i-Bu)
—C(O)NH(t-Bu)
—C(O)NHCH$_2$Ph
—C(O)NHCH$_2$CH=CH$_2$
—C(O)NHCH$_2$C≡CH
—C(O)NHC(Me)$_2$C≡CH
—C(O)NHCH$_2$CH$_2$F
—C(O)NHCH$_2$CHF$_2$
—C(O)NHCH$_2$CF$_3$
—C(O)NHCH(Me)CF$_3$
—C(O)NHCH$_2$CH$_2$CF$_3$
—C(O)NHCH$_2$CF$_2$CF$_3$
—C(O)NHCH$_2$CF$_2$CH$_3$
—C(O)NHCH$_2$CH$_2$CF$_2$CF$_3$
—C(O)NHCH(i-Pr)CF$_3$
—C(O)NHCH$_2$CH$_2$OMe
—C(O)NHCH$_2$OEt
—C(O)NHCH$_2$CH$_2$O(i-Pr)
—C(O)NHCH$_2$CH$_2$OEt
—C(O)NHCH$_2$CH$_2$CH$_2$OMe
—C(O)NHCH$_2$CH(Me)OMe
—C(O)NHCH(Et)CH$_2$OMe
—C(O)NHCH(Me)CH$_2$OMe
—C(O)NHCH$_2$CH$_2$S(O)Me
—C(O)NHCH$_2$CH$_2$SMe
—C(O)NHCH$_2$CH$_2$SEt
—C(O)NHCH$_2$CH$_2$SO$_2$Me
—C(O)NHCH$_2$CH$_2$SO$_2$Et
—C(O)NHCH$_2$CH$_2$S(O)Et
—C(O)NHCH$_2$CH$_2$S(O)(t-Bu)
—C(O)NHCH$_2$CH$_2$S(t-Bu)
—C(O)NHCH(Me)CH$_2$SMe
—C(O)NHCH$_2$CH$_2$SO$_2$(t-Bu)
—C(O)NHCH(Me)CH$_2$SO$_2$Me
—C(O)NHCH(Me)CH$_2$S(O)Me
—C(O)NHCH$_2$CH$_2$S(O)CH$_2$CF$_3$
—C(O)NHCH$_2$CH$_2$SCH$_2$CF$_3$
—C(O)NHCH$_2$CH$_2$SO$_2$CH$_2$CF$_3$
—C(O)NHCH$_2$CH$_2$SO$_2$CH$_2$CH$_2$CF$_3$
—C(O)NHCH$_2$CH$_2$SCH$_2$CH$_2$CF$_3$
—C(O)NHCH$_2$CH$_2$S(O)CH$_2$CH$_2$CF$_3$
—C(O)NHCH$_2$CN
—C(O)NHCH$_2$CH$_2$CN
—C(O)NHC(Me)$_2$CN
—C(O)NHCH$_2$CH$_2$N(i-Pr)$_2$
—C(O)NHCH$_2$CH$_2$N(Me)$_2$
—C(O)NHCH$_2$CH(OMe)$_2$
—C(O)NH(c-Pr)
—C(O)NH(c-Bu)
—C(O)NH(1-methylcyclopropyl)
—C(O)NH(3-methoxycyclobutyl)
—C(O)NHCH(Ph)(c-Pr)
—C(O)NHCH(Me)(c-Pr)
—C(O)NH(3-thietanyl)
—C(O)NH(3,3-difluorocyclobutyl)
—C(O)NH(3-oxetanyl)
—C(O)NHCH$_2$(oxiranyl)
—C(O)NH(3-thietanyl-1,1-dioxide)

TABLE I-5-continued

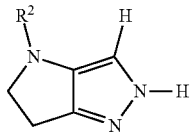

R[2]

—C(O)NH(3-thietanyl-1-oxide)
—C(O)NHCH$_2$(CH(—OC(Me)$_2$OCH$_2$—))
—C(O)NHCH$_2$(tetrahydro-2-furanyl)
—C(O)NHCH$_2$(2-furanyl)
—C(O)NH(tetrahydro-2-furanyl)
—C(O)NHCH$_2$(2-thienyl)
—C(O)NHCH$_2$(CH(—OCH$_2$CH$_2$O—)
—C(O)NHCH$_2$CO$_2$Me
—C(O)NHCH$_2$(2,2-difluorocyclopropyl)
—C(O)NHC(—CH$_2$CH$_2$—)CO$_2$Me
—C(O)NHCH(Me)CO$_2$Et
—C(O)NHCH(i-Pr)CO$_2$Me
—C(O)NHCH$_2$C(O)NHMe
—C(O)NHCH$_2$C(O)NMe$_2$
—C(O)NHCH(Me)C(O)NHMe
—C(O)NHCH(Me)C(O)NH(t-Bu)
—C(O)NHCH$_2$(6-CF$_3$-2-pyridinyl)
—C(O)NHCH(Me)C(O)NMe$_2$
—C(O)NHCH$_2$(3-CF$_3$-2-pyridinyl)
—C(O)NHCH$_2$(5-CF$_3$-2-pyrimidinyl)
—C(O)NHCH$_2$(4-CF$_3$-2-pyridinyl)
—C(O)NHCH$_2$(4-CF$_3$-2-pyrimidinyl)
—C(O)NHCH$_2$(6-methyl-2-pyridinyl)
—C(O)NHCH$_2$(5-CF$_3$-2-pyridinyl)
—C(O)NHCH$_2$(3-methyl-2-pyridinyl)
—C(O)NHCH$_2$(5-methyl-2-pyrimidinyl)
—C(O)NHCH$_2$(4-methyl-2-pyridinyl)
—C(O)NHCH$_2$(4-methyl-2-pyrimidinyl)
—C(O)NHCH$_2$(6-methoxy-2-pyridinyl)
—C(O)NHCH$_2$(5-methyl-2-pyridinyl)
—C(O)NHCH$_2$(3-methoxy-2-pyridinyl)
—C(O)NHCH$_2$(5-methoxy-2-pyrimidinyl)
—C(O)NHCH$_2$(4-methoxy-2-pyridinyl)
—C(O)NHCH$_2$(4-methoxy-2-pyrimidinyl)
—C(O)NHCH$_2$(5-pyrimidinyl)
—C(O)NHCH$_2$(5-methoxy-2-pyridinyl)
—C(O)NHCH$_2$(2-pyrimidinyl)
—C(O)NHCH$_2$(3-(OCF$_3$)phenyl)
—C(O)NHCH$_2$(6-bromo-2-pyridinyl)
—C(O)NHCH$_2$(5-methyl-2-pyrazinyl)
—C(O)NHCH$_2$(4-pyridinyl)
—C(O)NHCH$_2$(2-thiazolyl)
—C(O)NHPh
—C(O)NH(3-pyridinyl)
—C(O)NHCH$_2$(2-pyridinyl)
—C(O)NH(2-pyridinyl)
—C(O)NH(2-pyrazinyl)
—C(O)NHCH$_2$(3-pyridinyl)
—C(O)NH(4-pyridinyl)
—C(O)NH(4-CF$_3$-2-pyridinyl)
—C(O)NHCH$_2$(2-pyridinyl)
—C(O)NH(3-CF$_3$-2-pyridinyl)
—C(O)NH(4-CF$_3$-2-pyrimidinyl)
—C(O)NHCH$_2$CH$_2$(2-pyridinyl)
—C(O)NH(5-CF$_3$-2-pyridinyl)
—C(O)NH(5-CF$_3$-2-pyrazinyl)
—C(O)NH(6-CF$_3$-2-pyridinyl)
—C(O)NHCH$_2$CH$_2$N(—C(O)CH$_2$CH$_2$C(O)—)
—C(O)NHCH$_2$CH$_2$(1-imidazolyl)
—C(O)NH(5-CF$_3$-2-pyrimidinyl)
—C(O)NHNHCO$_2$Me
—C(O)NHNHC(O)NHMe
—C(O)NHNHC(O)NMe$_2$
3-methyl-2-pyridinyl
3-methoxy-2-pyridinyl
3-(trifluoromethyl)-2-pyridinyl
3-(CH(=NOMe))-2-pyridinyl
4-methyl-2-pyridinyl
4-methoxy-2-pyridinyl
4-(trifluoromethyl)-2-pyridinyl TABLE I-5-continued

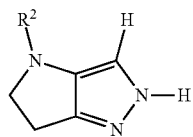

R²

4-(CH(=NOMe))-2-pyridinyl
5-methyl-2-pyridinyl
5-methoxy-2-pyridinyl
5-(trifluoromethyl)-2-pyridinyl
5-(CH(=NOMe))-2-pyridinyl
6-methyl-2-pyridinyl
6-methoxy-2-pyridinyl
6-(trifluoromethyl)-2-pyridinyl
6-(CH(=NOMe))-2-pyridinyl
2-methyl-3-pyridinyl
2-methoxy-3-pyridinyl
2-(trifluoromethyl)-3-pyridinyl
2-(CH(=NOMe))-3-pyridinyl
4-methyl-3-pyridinyl
4-methoxy-3-pyridinyl
4-(trifluoromethyl)-3-pyridinyl
4-(CH(=NOMe))-3-pyridinyl
5-methyl-3-pyridinyl
5-methoxy-3-pyridinyl
5-(trifluoromethyl)-3-pyridinyl
5-(CH(=NOMe))-3-pyridinyl
6-methyl-3-pyridinyl
6-methoxy-3-pyridinyl
6-(trifluoromethyl)-3-pyridinyl
6-(CH(=NOMe))-3-pyridinyl
2-methyl-4-pyridinyl
2-methoxy-4-pyridinyl
2-(trifluoromethyl)-4-pyridinyl
2-(CH(=NOMe))-4-pyridinyl
3-methyl-4-pyridinyl
3-methoxy-4-pyridinyl
3-(trifluoromethyl)-4-pyridinyl
3-(CH(=NOMe))-4-pyridinyl
3-methyl-2-pyrazinyl
3-methoxy-2-pyrazinyl
3-(trifluoromethyl)-2-pyrazinyl
3-(CH(=NOMe))-2-pyrazinyl
5-methyl-2-pyrazinyl
5-methoxy-2-pyrazinyl
5-(trifluoromethyl)-2-pyrazinyl
5-(CH(=NOMe))-2-pyrazinyl
6-methyl-2-pyrazinyl
6-methoxy-2-pyrazinyl
6-(trifluoromethyl)-2-pyrazinyl
6-(CH(=NOMe))-2-pyrazinyl
4-methyl-2-pyrimidinyl
4-methoxy-2-pyrimidinyl
4-(trifluoromethyl)-2-pyrimidinyl
4-(CH(=NOMe))-2-pyrimidinyl
5-methyl-2-pyrimidinyl
5-methoxy-2-pyrimidinyl
5-(trifluoromethyl)-2-pyrimidinyl
5-(CH(=NOMe))-2-pyrimidinyl
2-methyl-4-pyrimidinyl
2-methoxy-4-pyrimidinyl
2-(trifluoromethyl)-4-pyrimidinyl
2-(CH(=NOMe))-4-pyrimidinyl
5-methyl-4-pyrimidinyl
5-methoxy-4-pyrimidinyl
5-(trifluoromethyl)-4-pyrimidinyl
5-(CH(=NOMe))-4-pyrimidinyl
6-methyl-4-pyrimidinyl
6-methoxy-4-pyrimidinyl
6-(trifluoromethyl)-4-pyrimidinyl
6-(CH(=NOMe))-4-pyrimidinyl
3-methyl-1-pyrazolyl
3-methoxy-1-pyrazolyl
3-(trifluoromethyl)-1-pyrazolyl
3-(CH(=NOMe))-1-pyrazolyl
4-methyl-1-pyrazolyl TABLE I-5-continued

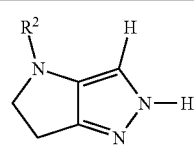

R²

4-methoxy-1-pyrazolyl
4-(trifluoromethyl)-1-pyrazolyl
4-(CH(=NOMe))-1-pyrazolyl
5-methyl-1-pyrazolyl
5-methoxy-1-pyrazolyl
5-(trifluoromethyl)-1-pyrazolyl
5-(CH(=NOMe))-1-pyrazolyl
4-methyl-1,2,3-triazin-2-yl
4-methoxy-1,2,3-triazin-2-yl
4-(trifluoromethyl)-1,2,3-triazin-2-yl
4-(CH(=NOMe))-1,2,3-triazin-2-yl
6-(2-pyrimidinyl)-2-pyridinyl
2-(2-pyridinyl)-4-thiazolyl
2-(2-thiazolyl)-4-thiazolyl
2-(2-pyrimidinyl)ethynyl
1,3,4-oxadiazol-2-yl
tetrahydro-3-furanyl
tetrahydro-2-furanyl
4,5-dihydro-3-isoxazolyl
3-isoxazolyl
phenyl
2-(trifluoromethyl)phenyl
3-(trifluoromethyl)phenyl
4-(trifluoromethyl)phenyl Table I-6

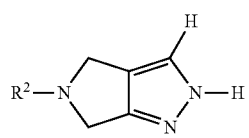

Table I-6 is identical to Table I-5, except that the structure shown under the heading "TABLE I-5" is replaced by the structure shown above.

Table I-7

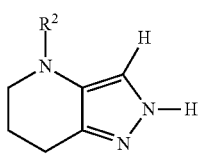

Table I-7 is identical to Table I-5, except that the structure shown under the heading "TABLE I-5" is replaced by the structure shown above.

Table I-8

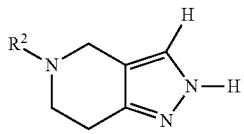

Table I-8 is identical to Table I-5, except that the structure shown under the heading "TABLE I-5" is replaced by the structure shown above.

By the procedures described herein together with methods known in the art, the following compounds of Tables 1 to 4c can be prepared. The following abbreviations may be used in the Tables which follow: t means tertiary, s means secondary, i means iso, c means cyclo, Me means methyl, Et means ethyl, Pr means propyl, Bu means butyl, Ph means phenyl, OMe means methoxy, OEt means ethoxy, SMe means methylthio, SEt means ethylthio, —CN means cyano, Ph means phenyl, Py means pyridinyl, —NO$_2$ means nitro, S(O)Me means methylsulfinyl, and S(O)$_2$Me means methylsulfonyl.

A "—" at the beginning of a fragment definition denotes the attachment point of said fragment to the remainder of the molecule; for example, "—CH$_2$CH$_2$OMe" denotes the fragment 2-methoxyethyl. Cyclic fragments are represented by the use of two "—" within parentheses; for example, the fragment 1-pyrrolidinyl is represented by "N(—CH$_2$CH$_2$CH$_2$CH$_2$—)", wherein a nitrogen atom is bonded to both terminal carbon atoms of the four-carbon chain, as illustrated below.

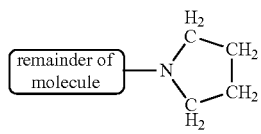

TABLE 1a

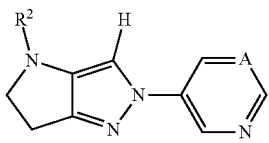

| R$_2$ |
|---|
| —C(O)Me |
| —C(O)Et |
| —C(O)Pr |
| —C(O)(i-Pr) |
| —C(O)CH$_2$(c-Pr) |
| —C(O)CH(Me)(c-Pr) |
| —C(O)Bu |
| —C(O)(s-Bu) |
| —C(O)(i-Bu) |
| —C(O)(t-Bu) |
| —C(O)CH$_2$Ph |
| —C(O)CH$_2$CH═CH$_2$ |
| —C(O)CH$_2$C≡CH |
| —C(O)C(Me)$_2$C≡CH |
| —C(O)CH$_2$CH$_2$F |
| —C(O)CH$_2$CHF$_2$ |
| —C(O)CH$_2$CF$_3$ |

TABLE 1a-continued

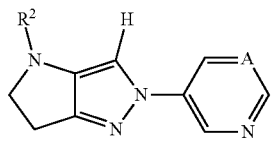

| R$_2$ |
|---|
| —C(O)CH(Me)CF$_3$ |
| —C(O)CH$_2$CH$_2$CF$_3$ |
| —C(O)CH$_2$CF$_2$CF$_3$ |
| —C(O)CH$_2$CF$_2$CH$_3$ |
| —C(O)CH$_2$CH$_2$CF$_2$CF$_3$ |
| —C(O)CH(i-Pr)CF$_3$ |
| —C(O)CH$_2$CH$_2$OMe |
| —C(O)CH$_2$OEt |
| —C(O)CH$_2$CH$_2$O(i-Pr) |
| —C(O)CH$_2$CH$_2$OEt |
| —C(O)CH$_2$CH$_2$CH$_2$OMe |
| —C(O)CH$_2$CH(Me)OMe |
| —C(O)CH(Et)CH$_2$OMe |
| —C(O)CH(Me)CH$_2$OMe |
| —C(O)CH$_2$CH$_2$S(O)Me |
| —C(O)CH$_2$CH$_2$SMe |
| —C(O)CH$_2$CH$_2$SEt |
| —C(O)CH$_2$CH$_2$SO$_2$Me |
| —C(O)CH$_2$CH$_2$SO$_2$Et |
| —C(O)CH$_2$CH$_2$S(O)Et |
| —C(O)CH$_2$CH$_2$S(O)(t-Bu) |
| —C(O)CH$_2$CH$_2$S(t-Bu) |
| —C(O)CH(Me)CH$_2$SMe |
| —C(O)CH$_2$CH$_2$SO$_2$(t-Bu) |
| —C(O)CH(Me)CH$_2$SO$_2$Me |
| —C(O)CH(Me)CH$_2$S(O)Me |
| —C(O)CH$_2$CH$_2$S(O)CH$_2$CF$_3$ |
| —C(O)CH$_2$CH$_2$SCH$_2$CF$_3$ |
| —C(O)CH$_2$CH$_2$SO$_2$CH$_2$CF$_3$ |
| —C(O)CH$_2$CH$_2$SO$_2$CH$_2$CH$_2$CF$_3$ |
| —C(O)CH$_2$CH$_2$SCH$_2$CH$_2$CF$_3$ |
| —C(O)CH$_2$CH$_2$S(O)CH$_2$CH$_2$CF$_3$ |
| —C(O)CH$_2$CN |
| —C(O)CH$_2$CH$_2$CN |
| —C(O)C(Me)$_2$CN |
| —C(O)CH$_2$CH$_2$N(i-Pr)$_2$ |
| —C(O)CH$_2$CH$_2$N(Me)$_2$ |
| —C(O)CH$_2$CH(OMe)$_2$ |
| —C(O)(c-Pr) |
| —C(O)(c-Bu) |
| —C(O)(1-methylcyclopropyl) |
| —C(O)(3-methoxycyclobutyl) |
| —C(O)CH(Ph)(c-Pr) |
| —C(O)CH(Me)(c-Pr) |
| —C(O)(3-thietanyl) |
| —C(O)(3,3-difluorocyclobutyl) |
| —C(O)(3-oxetanyl) |
| —C(O)CH$_2$(oxiranyl) |
| —C(O)(3-thietanyl-1,1-dioxide) |
| —C(O)(3-thietanyl-1-oxide) |
| —C(O)CH$_2$(CH(—OC(Me)$_2$OCH$_2$—)) |
| —C(O)CH$_2$(tetrahydro-2-furanyl) |
| —C(O)CH$_2$(2-furanyl) |
| —C(O)(tetrahydro-2-furanyl) |
| —C(O)CH$_2$(2-thienyl) |
| —C(O)CH$_2$(CH(—OCH$_2$CH$_2$O—) |
| —C(O)CH$_2$CO$_2$Me |
| —C(O)CH$_2$(2,2-difluorocyclopropyl) |
| —C(O)C(—CH$_2$CH$_2$—)CO$_2$Me |
| —C(O)CH(Me)CO$_2$Et |
| —C(O)CH(i-Pr)CO$_2$Me |
| —C(O)CH$_2$C(O)NHMe |
| —C(O)CH$_2$C(O)NMe$_2$ |
| —C(O)CH(Me)C(O)NHMe |
| —C(O)CH(Me)C(O)NH(t-Bu) |
| —C(O)CH$_2$(6-CF$_3$-2-pyridinyl) |
| —C(O)CH(Me)C(O)NMe$_2$ |
| —C(O)CH$_2$(3-CF$_3$-2-pyridinyl) |
| —C(O)CH$_2$(5-CF$_3$-2-pyrimidinyl) |
| —C(O)CH$_2$(4-CF$_3$-2-pyridinyl) |

TABLE 1a-continued

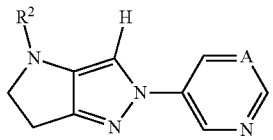

R₂

—C(O)CH₂(4-CF₃-2-pyrimidinyl)
—C(O)CH₂(6-methyl-2-pyridinyl)
—C(O)CH₂(5-CF₃-2-pyridinyl)
—C(O)CH₂(3-methyl-2-pyridinyl)
—C(O)CH₂(5-methyl-2-pyrimidinyl)
—C(O)CH₂(4-methyl-2-pyridinyl)
—C(O)CH₂(4-methyl-2-pyrimidinyl)
—C(O)CH₂(6-methoxy-2-pyridinyl)
—C(O)CH₂(5-methyl-2-pyridinyl)
—C(O)CH₂(3-methoxy-2-pyridinyl)
—C(O)CH₂(5-methoxy-2-pyrimidinyl)
—C(O)CH₂(4-methoxy-2-pyridinyl)
—C(O)CH₂(4-methoxy-2-pyrimidinyl)
—C(O)CH₂(5-pyrimidinyl)
—C(O)CH₂(5-methoxy-2-pyridinyl)
—C(O)CH₂(2-pyrimidinyl)
—C(O)CH₂(3-(OCF₃)phenyl)
—C(O)CH₂(6-bromo-2-pyridinyl)
—C(O)CH₂(5-methyl-2-pyrazinyl)
—C(O)CH₂(4-pyridinyl)
—C(O)CH₂(2-thiazolyl)
—C(O)Ph
—C(O)(3-pyridinyl)
—C(O)CH₂(2-pyridinyl)
—C(O)(2-pyridinyl)
—C(O)(2-pyrazinyl)
—C(O)CH₂(3-pyridinyl)
—C(O)(4-pyridinyl)
—C(O)(4-CF₃-2-pyridinyl)
—C(O)CH₂(Ph)(2-pyridinyl)
—C(O)(3-CF₃-2-pyridinyl)
—C(O)(4-CF₃-2-pyrimidinyl)
—C(O)CH₂CH₂CH₂(2-pyridinyl)
—C(O)(5-CF₃-2-pyridinyl)
—C(O)(5-CF₃-2-pyrazinyl)
—C(O)(6-CF₃-2-pyridinyl)
—C(O)CH₂CH₂N(—C(O)CH₂CH₂C(O)—)
—C(O)CH₂CH₂CH₂(1-imidazolyl)
—C(O)(5-CF₃-2-pyrimidinyl)
—C(O)CH(—C(O)OCH₂CH₂—)
—C(O)NHMe
—C(O)NHEt
—C(O)NHPr
—C(O)NH(i-Pr)
—C(O)NHCH₂(c-Pr)
—C(O)NHCH(Me)(c-Pr)
—C(O)NHBu
—C(O)NH(s-Bu)
—C(O)NH(i-Bu)
—C(O)NH(t-Bu)
—C(O)NHCH₂Ph
—C(O)NHCH₂CH=CH₂
—C(O)NHCH₂C≡CH
—C(O)NHC(Me)₂C≡CH
—C(O)NHCH₂CH₂F
—C(O)NHCH₂CHF₂
—C(O)NHCH₂CF₃
—C(O)NHCH(Me)CF₃
—C(O)NHCH₂CH₂CF₃
—C(O)NHCH₂CF₂CF₃
—C(O)NHCH₂CF₂CH₃
—C(O)NHCH₂CH₂CF₂CF₃
—C(O)NHCH(i-Pr)CF₃
—C(O)NHCH₂CH₂OMe
—C(O)NHCH₂CH₂OEt
—C(O)NHCH₂CH₂O(i-Pr)
—C(O)NHCH₂CH₂OEt
—C(O)NHCH₂CH₂CH₂OMe
—C(O)NHCH₂CH(Me)OMe
—C(O)NHCH(Et)CH₂OMe TABLE 1a-continued

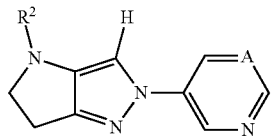

R₂

—C(O)NHCH(Me)CH₂OMe
—C(O)NHCH₂CH₂S(O)Me
—C(O)NHCH₂CH₂SMe
—C(O)NHCH₂CH₂SEt
—C(O)NHCH₂CH₂SO₂Me
—C(O)NHCH₂CH₂SO₂Et
—C(O)NHCH₂CH₂S(O)Et
—C(O)NHCH₂CH₂S(O)(t-Bu)
—C(O)NHCH₂CH₂S(t-Bu)
—C(O)NHCH(Me)CH₂SMe
—C(O)NHCH₂CH₂SO₂(t-Bu)
—C(O)NHCH(Me)CH₂SO₂Me
—C(O)NHCH(Me)CH₂S(O)Me
—C(O)NHCH₂CH₂S(O)CH₂CF₃
—C(O)NHCH₂CH₂SCH₂CF₃
—C(O)NHCH₂CH₂SO₂CH₂CF₃
—C(O)NHCH₂CH₂SO₂CH₂CH₂CF₃
—C(O)NHCH₂CH₂SCH₂CH₂CF₃
—C(O)NHCH₂CH₂S(O)CH₂CH₂CF₃
—C(O)NHCH₂CN
—C(O)NHCH₂CH₂CN
—C(O)NHC(Me)₂CN
—C(O)NHCH₂CH₂N(i-Pr)₂
—C(O)NHCH₂CH₂N(Me)₂
—C(O)NHCH₂CH(OMe)₂
—C(O)NH(c-Pr)
—C(O)NH(c-Bu)
—C(O)NH(1-methylcyclopropyl)
—C(O)NH(3-methoxycyclobutyl)
—C(O)NHCH(Ph)(c-Pr)
—C(O)NHCH(Me)(c-Pr)
—C(O)NH(3-thietanyl)
—C(O)NH(3,3-difluorocyclobutyl)
—C(O)NH(3-oxetanyl)
—C(O)NHCH₂(oxiranyl)
—C(O)NH(3-thietanyl-1,1-dioxide)
—C(O)NH(3-thietanyl-1-oxide)
—C(O)NHCH₂(CH(—OC(Me)₂OCH₂—))
—C(O)NHCH₂(tetrahydro-2-furanyl)
—C(O)NHCH₂(2-furanyl)
—C(O)NH(tetrahydro-2-furanyl)
—C(O)NHCH₂(2-thienyl)
—C(O)NHCH₂(CH(—OCH₂CH₂O—)
—C(O)NHCH₂CO₂Me
—C(O)NHCH₂(2,2-difluorocyclopropyl)
—C(O)NHC(—CH₂CH₂—)CO₂Me
—C(O)NHCH(Me)CO₂Et
—C(O)NHCH(i-Pr)CO₂Me
—C(O)NHCH₂C(O)NHMe
—C(O)NHCH₂C(O)NMe₂
—C(O)NHCH(Me)C(O)NHMe
—C(O)NHCH(Me)C(O)NH(t-Bu)
—C(O)NHCH₂(6-CF₃-2-pyridinyl)
—C(O)NHCH(Me)C(O)NMe₂
—C(O)NHCH₂(3-CF₃-2-pyridinyl)
—C(O)NHCH₂(5-CF₃-2-pyrimidinyl)
—C(O)NHCH₂(4-CF₃-2-pyridinyl)
—C(O)NHCH₂(4-CF₃-2-pyrimidinyl)
—C(O)NHCH₂(6-methyl-2-pyridinyl)
—C(O)NHCH₂(5-CF₃-2-pyridinyl)
—C(O)NHCH₂(3-methyl-2-pyridinyl)
—C(O)NHCH₂(5-methyl-2-pyrimidinyl)
—C(O)NHCH₂(4-methyl-2-pyridinyl)
—C(O)NHCH₂(4-methyl-2-pyrimidinyl)
—C(O)NHCH₂(6-methoxy-2-pyridinyl)
—C(O)NHCH₂(5-methyl-2-pyridinyl)
—C(O)NHCH₂(3-methoxy-2-pyridinyl)
—C(O)NHCH₂(5-methoxy-2-pyrimidinyl)
—C(O)NHCH₂(4-methoxy-2-pyridinyl)
—C(O)NHCH₂(4-methoxy-2-pyrimidinyl)

TABLE 1a-continued

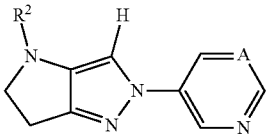

R_2

—C(O)NHCH$_2$(5-pyrimidinyl)
—C(O)NHCH$_2$(5-methoxy-2-pyridinyl)
—C(O)NHCH$_2$(2-pyrimidinyl)
—C(O)NHCH$_2$(3-(OCF$_3$)phenyl)
—C(O)NHCH$_2$(6-bromo-2-pyridinyl)
—C(O)NHCH$_2$(5-methyl-2-pyrazinyl)
—C(O)NHCH$_2$(4-pyridinyl)
—C(O)NHCH$_2$(2-thiazolyl)
—C(O)NHPh
—C(O)NH(3-pyridinyl)
—C(O)NHCH$_2$(2-pyridinyl)
—C(O)NH(2-pyridinyl)
—C(O)NH(2-pyrazinyl)
—C(O)NHCH$_2$(3-pyridinyl)
—C(O)NH(4-pyridinyl)
—C(O)NH(4-CF$_3$-2-pyridinyl)
—C(O)NHCH$_2$CH$_2$(2-pyridinyl)
—C(O)NH(3-CF$_3$-2-pyridinyl)
—C(O)NH(4-CF$_3$-2-pyrimidinyl)
—C(O)NHCH$_2$CH$_2$CH$_2$(2-pyridinyl)
—C(O)NH(5-CF$_3$-2-pyridinyl)
—C(O)NH(5-CF$_3$-2-pyrazinyl)
—C(O)NH(6-CF$_3$-2-pyridinyl)
—C(O)NHCH$_2$CH$_2$N(—C(O)CH$_2$CH$_2$C(O)—)
—C(O)NHCH$_2$CH$_2$CH$_2$(1-imidazolyl)
—C(O)NH(5-CF$_3$-2-pyrimidinyl)
—C(O)NHNHCO$_2$Me
—C(O)NHNHC(O)NHMe
—C(O)NHNHC(O)NMe$_2$
3-methyl-2-pyridinyl
3-methoxy-2-pyridinyl
3-(trifluoromethyl)-2-pyridinyl
3-(CH(=NOMe))-2-pyridinyl
4-methyl-2-pyridinyl
4-methoxy-2-pyridinyl
4-(trifluoromethyl)-2-pyridinyl
4-(CH(=NOMe))-2-pyridinyl
5-methyl-2-pyridinyl
5-methoxy-2-pyridinyl
5-(trifluoromethyl)-2-pyridinyl
5-(CH(=NOMe))-2-pyridinyl
6-methyl-2-pyridinyl
6-methoxy-2-pyridinyl
6-(trifluoromethyl)-2-pyridinyl
6-(CH(=NOMe))-2-pyridinyl
2-methyl-3-pyridinyl
2-methoxy-3-pyridinyl
2-(trifluoromethyl)-3-pyridinyl
2-(CH(=NOMe))-3-pyridinyl
4-methyl-3-pyridinyl
4-methoxy-3-pyridinyl
4-(trifluoromethyl)-3-pyridinyl
4-(CH(=NOMe))-3-pyridinyl
5-methyl-3-pyridinyl
5-methoxy-3-pyridinyl
5-(trifluoromethyl)-3-pyridinyl
5-(CH(=NOMe))-3-pyridinyl
6-methyl-3-pyridinyl
6-methoxy-3-pyridinyl
6-(trifluoromethyl)-3-pyridinyl
6-(CH(=NOMe))-3-pyridinyl
2-methyl-4-pyridinyl
2-methoxy-4-pyridinyl
2-(trifluoromethyl)-4-pyridinyl
2-(CH(=NOMe))-4-pyridinyl
3-methyl-4-pyridinyl
3-methoxy-4-pyridinyl
3-(trifluoromethyl)-4-pyridinyl
3-(CH(=NOMe))-4-pyridinyl
3-methyl-2-pyrazinyl TABLE 1a-continued

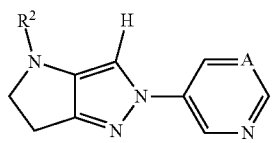

R_2

3-methoxy-2-pyrazinyl
3-(trifluoromethyl)-2-pyrazinyl
3-(CH(=NOMe))-2-pyrazinyl
5-methyl-2-pyrazinyl
5-methoxy-2-pyrazinyl
5-(trifluoromethyl)-2-pyrazinyl
5-(CH(=NOMe))-2-pyrazinyl
6-methyl-2-pyrazinyl
6-methoxy-2-pyrazinyl
6-(trifluoromethyl)-2-pyrazinyl
6-(CH(=NOMe))-2-pyrazinyl
4-methyl-2-pyrimidinyl
4-methoxy-2-pyrimidinyl
4-(trifluoromethyl)-2-pyrimidinyl
4-(CH(=NOMe))-2-pyrimidinyl
5-methyl-2-pyrimidinyl
5-methoxy-2-pyrimidinyl
5-(trifluoromethyl)-2-pyrimidinyl
5-(CH(=NOMe))-2-pyrimidinyl
2-methyl-4-pyrimidinyl
2-methoxy-4-pyrimidinyl
2-(trifluoromethyl)-4-pyrimidinyl
2-(CH(=NOMe))-4-pyrimidinyl
5-methyl-4-pyrimidinyl
5-methoxy-4-pyrimidinyl
5-(trifluoromethyl)-4-pyrimidinyl
5-(CH(=NOMe))-4-pyrimidinyl
6-methyl-4-pyrimidinyl
6-methoxy-4-pyrimidinyl
6-(trifluoromethyl)-4-pyrimidinyl
6-(CH(=NOMe))-4-pyrimidinyl
3-methyl-1-pyrazolyl
3-methoxy-1-pyrazolyl
3-(trifluoromethyl)-1-pyrazolyl
3-(CH(=NOMe))-1-pyrazolyl
4-methyl-1-pyrazolyl
4-methoxy-1-pyrazolyl
4-(trifluoromethyl)-1-pyrazolyl
4-(CH(=NOMe))-1-pyrazolyl
5-methyl-1-pyrazolyl
5-methoxy-1-pyrazolyl
5-(trifluoromethyl)-1-pyrazolyl
5-(CH(=NOMe))-1-pyrazolyl
4-methyl-1,2,3-triazin-2-yl
4-methoxy-1,2,3-triazin-2-yl
4-(trifluoromethyl)-1,2,3-triazin-2-yl
4-(CH(=NOMe))-1,2,3-triazin-2-yl
6-(2-pyrimidinyl)-2-pyridinyl
2-(2-pyridinyl)-4-thiazolyl
2-(2-thiazolyl)-4-thiazolyl
2-(2-pyrimidinyl)ethynyl
1,3,4-oxadiazol-2-yl
tetrahydro-3-furanyl
tetrahydro-2-furanyl
4,5-dihydro-3-isoxazolyl
3-isoxazolyl
phenyl
2-(trifluoromethyl)phenyl
3-(trifluoromethyl)phenyl
4-(trifluoromethyl)phenyl Table 1b Table 1b is identical to Table 1a, except that A is CF.

Table 1c

Table 1c is identical to Table 1a, except that A is N.

Table 2a

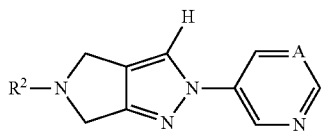

Table 2a is identical to Table 1a, except that the structure shown under the heading "TABLE 1a" is replaced by the structure shown above.

Table 2b

Table 2b is identical to Table 2a, except that A is CF.

Table 2c

Table 2c is identical to Table 2a, except that A is N.

Table 3a

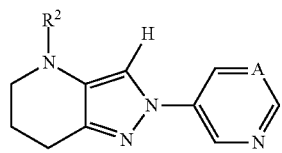

Table 3a is identical to Table 1a, except that the structure shown under the heading "TABLE 1a" is replaced by the structure shown above.

Table 3b

Table 3b is identical to Table 3a, except that A is CF.

Table 3c

Table 3c is identical to Table 3a, except that A is N.

Table 4a

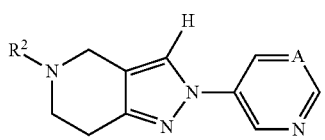

Table 4a is identical to Table 1a, except that the structure shown under the heading "TABLE 1a" is replaced by the structure shown above.

Table 4b

Table 4b is identical to Table 4a, except that A is CF.

Table 4c

Table 4c is identical to Table 4a, except that A is N.

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil in water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil in water emulsion, flowable concentrate and suspoemulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethylphosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters alkyl and aryl benzoates, γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
| --- | --- |
| Compound 14 | 98.5% |
| silica aerogel | 0.5% |
| synthetic amorphous fine silica | 1.0% |

Example B

| Wettable Powder | |
| --- | --- |
| Compound 15 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| Compound 20 | 10.0% |
| attapulgite granules (low volatile matter, 0.71/0.30 mm; U.S.S. No. 25-50 sieves) | 90.0% |

Example D

| Extruded Pellet | |
| --- | --- |
| Compound 22 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 23 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 47 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 48 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| Compound 51 | 2.5% |
| pyrrolidone-styrene copolymer | 4.8% |
| tristyrylphenyl 16-ethoxylate | 2.3% |
| talc | 0.8% |
| corn starch | 5.0% |
| slow-release fertilizer | 36.0% |
| kaolin | 38.0% |
| water | 10.6% |

Example I

| Suspension Concentrate | |
|---|---|
| compound 54 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| compound 14 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| compound 15 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| compound 20 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-b enzisothiazolin-3-one | 0.1% |
| aromatic petroleum based hydrocarbon | 20.0% |
| water | 53.7% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, INVICTA RR2 PRO™, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

Nonagronomic uses of the present compounds and compositions also include protecting human and animal health by controlling invertebrate pests that are parasitic or transmit infectious diseases. The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. Compounds and compositions of the present invention are suitable for systemic and/or non-systemic control of infestation or infection by parasites on animals. Compounds and compositions of the present invention are particularly suitable for combating external parasitic or disease transmitting pests. Compounds and compositions of the present invention are suitable for combating parasites that infest agricultural working animals, such as cattle, sheep, goats, horses, pigs, donkeys, camels, buffalos, rabbits, hens, turkeys, ducks, geese and bees; pet animals and domestic animals such as dogs, cats, pet birds and aquarium fish; as well as so-called experimental animals, such as hamsters, guinea pigs, rats and mice. By combating these parasites, fatalities and performance reduction (in terms of meat, milk, wool, skins, eggs, honey, etc.) are reduced, so that applying a composition comprising a compound of the present invention allows more economic and simple husbandry of animals.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera frugiperda* J. E. Smith), beet armyworm (*Spodoptera exigua* Hübner), cotton leafworm (*Spodoptera littoralis* Boisduval), yellowstriped armyworm (*Spodoptera ornithogalli* Guenée), black cutworm (*Agrotis ipsilon* Hufnagel), velvetbean caterpillar (*Anticarsia gemmatalis* Hübner), green fruitworm (*Lithophane antennata* Walker), cabbage armyworm (*Barathra brassicae* Linnaeus), soybean looper (*Pseudoplusia includens* Walker), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis* Walker), sugarcane stem borer (*Chilo infuscatellus* Snellen), tomato small borer (*Neoleucinodes elegantalis* Guenée), green leafroller (*Cnaphalocrocis medinalis*), grape leaffolder (*Desmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infuscatellus* Snellen), white stem borer (*Scirpophaga innotata* Walker), top shoot borer (*Scirpophaga nivella* Fabricius), dark-headed rice borer (*Chilo polychrysus* Meyrick), striped riceborer (*Chilo suppressalis* Walker), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdytolopha aurantiana* Lima), redbanded leafroller (*Argyrotaenia velutinana* Walker), obliquebanded leafroller (*Choristoneura rosaceana* Harris), light brown apple moth (*Epiphyas postvittana* Walker), European grape berry moth (*Eupoecilia ambiguella* Hübner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermüller)); and many other economically important lepidoptera (e.g., diamondback moth (*Plutella xylostella* Linnaeus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafminer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus vestitus*), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order Isoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotermes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Stiophilus granarius*), Indian meal moth (*Plodia interpunctella*), Mediterranean flour beetle (*Ephestia kuhniella*) and flat or rusty grain beetle (*Cryptolestis ferrugineus*).

Compounds of the present invention may have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Compounds of the invention may have activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus teterrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermüller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xylostella* Linnaeus (diamondback moth), *Spodoptera exigua* Hübner (beet armyworm), *Spodoptera litura* Fabricius (tobacco cutworm, cluster caterpillar), *Spodoptera frugiperda* J. E. Smith (fall armyworm), *Trichoplusia ni* Hübner (cabbage looper) and *Tuta absoluta* Meyrick (tomato leafminer)).

Compounds of the invention have significant activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis plantaginea* Paaserini (rosy apple aphid), *Eriosoma lanigerum* Hausmann (woolly apple aphid), *Hyalopterus pruni* Geoffroy (mealy plum aphid), *Lipaphis erysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia tabaci* Gennadius (tobacco whitefly, sweetpotato whitefly), *Bemisia argentifolii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatellus* Fallen (smaller brown planthopper), *Macrolestes quadrilineatus* Forbes (aster leafhopper), *Nephotettix cinticeps* Uhler (green leafhopper), *Nephotettix nigropictus* Stål (rice leafhopper), *Nilaparvata lugens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erythroneoura* spp. (grape leafhoppers); *Magicidada septendecim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Halymorpha halys* Stål (brown marmorated stink bug), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnax* Fabricius (rice stink bug), *Oncopeltus fasciatus* Dallas (large milkweed bug), *Pseudatomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of compounds of this invention for controlling western flower thrips (*Frankliniella occidentalis*). Of note is use of compounds of this invention for controlling potato leafhopper (*Empoasca fabae*). Of note is use of compounds of this invention for controlling cotton melon aphid (*Aphis gossypii*). Of note is use of compounds of this invention for controlling green peach aphid (*Myzus persicae*). Of note is use of compounds of this invention for controlling sweetpotato whitefly (*Bemisia tabaci*).

Compounds of the present invention may also be useful for increasing vigor of a crop plant. This method comprises contacting the crop plant (e.g., foliage, flowers, fruit or roots) or the seed from which the crop plant is grown with a compound of Formula 1 in amount sufficient to achieve the desired plant vigor effect (i.e. biologically effective amount). Typically the compound of Formula 1 is applied in a formulated composition. Although the compound of Formula 1 is often applied directly to the crop plant or its seed, it can also be applied to the locus of the crop plant, i.e. the environment of the crop plant, particularly the portion of the environment in close enough proximity to allow the compound of Formula 1 to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula 1.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and (e) increased ability of the crop to withstand environmental stresses such as exposure to thermal extremes, suboptimal moisture or phytotoxic chemicals.

The compounds of the present invention may increase the vigor of treated plants compared to untreated plants by killing or otherwise preventing feeding of phytophagous invertebrate pests in the environment of the plants. In the absence of such control of phytophagous invertebrate pests, the pests reduce plant vigor by consuming plant tissues or sap, or transmitting plant pathogens such as viruses. Even in the absence of phytophagous invertebrate pests, the compounds of the invention may increase plant vigor by modifying metabolism of plants. Generally, the vigor of a crop plant will be most significantly increased by treating the plant with a compound of the invention if the plant is grown in a nonideal environment, i.e. an environment comprising one or more aspects adverse to the plant achieving the full genetic potential it would exhibit in an ideal environment.

Of note is a method for increasing vigor of a crop plant wherein the crop plant is grown in an environment comprising phytophagous invertebrate pests. Also of note is a method for increasing vigor of a crop plant wherein the crop plant is grown in an environment not comprising phytophagous invertebrate pests. Also of note is a method for increasing vigor of a crop plant wherein the crop plant is grown in an environment comprising an amount of moisture less than ideal for supporting growth of the crop plant. Of note is a method for increasing vigor of a crop plant wherein the crop is rice. Also of note is a method for increasing vigor of a crop plant wherein the crop is maize (corn). Also of note is a method for increasing vigor of a crop plant wherein the crop is soybean.

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1H-pyrazole-5-carboxamide), cyclorprothrin, cycloxaprid ((5S,8R)-1-[(6-chloro-3-pyridinyl)methyl]-2,3,5,6,7,8-hexahydro-9-nitro-5,8-Epoxy-1H-imidazo[1,2-a]azepine) cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), flufensulfone (5-chloro-2-[(3,4,4-trifluoro-3-buten-1-yl)sulfonyl]thiazole), fluhexafon, fluopyram, flupiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), fluvalinate, tau-fluvalinate, fonophos, formetanate, fosthiazate, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hexythiazox, hydramethylnon, imidacloprid, indoxacarb, insecticidal soaps, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiodicarb, methomyl, methoprene, methoxychlor, metofluthrin, methoxyfenozide, metofluthrin, monocrotophos, monofluorothrin ([2,3,5,6-tetrafluoro-4-(methoxymethyl)phenyl]methyl 3-(2-cyano-1-propen-1-yl)-2,2-dimethylcyclopropanecarboxylate), nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), pymetrozine, pyrafluprole, pyrethrin, pyridaben, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene)benzeneacetate), pyriprole, pyriproxyfen, rotenone, ryanodine, silafluofen, spinetoram, spinosad, spirodiclofen, spiromesifen, spirotetramat, sulprofos, sulfoxaflor (N-[methyloxido[1-[6-(trifluoromethyl)-3-pyridinyl]ethyl]-λ$^{4}$-sulfanylidene]cyanamide), tebufenozide, tebufenpyrad, teflubenzuron, tefluthrin, terbufos, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, afidopyropen, amitraz, avermectin, azadirachtin, benfuracarb, bensultap, bifenthrin, buprofezin, cadusafos, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiodicarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nucleo polyhedrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, acetylcholinesterase (AChE) inhibitors such as the carbamates methomyl, oxamyl, thiodicarb, triazamate, and the organophosphates chlorpyrifos; GABA-gated chloride channel antagonists such as the cyclodienes dieldrin and endosulfan, and the phenylpyrazoles ethiprole and fipronil; sodium channel modulators such as the pyrethroids bifenthrin, cyfluthrin, beta-cyfluthrin, cyhalothrin, lambda-cyhalothrin, cypermethrin, deltamethrin, dimefluthrin, esfenvalerate, metofluthrin and profluthrin; nicotinic acetylcholinereceptor (nAChR) agonists such as the neonicotinoids acetamiprid, clothianidin, dinotefuran, imidacloprid, nitenpyram, nithiazine, thiacloprid, and thiamethoxam, and sulfoxaflor; nicotinic acetylcholine receptor (nAChR) allosteric activators such as the spinosyns spinetoram and spinosad; chloride channel activators such as the avermectins abamectin and emamectin; juvenile hormone mimics such as diofenolan, methoprene, fenoxycarb and pyriproxyfen; selective homopteran feeding blockers such as pymetrozine and flonicamid; mite growth inhibitors such as etoxazole; inhibitors of mitochondrial ATP synthase such as propargite; ucouplers of oxidative phosphorylation via disruption of the proton gradient such as chlorfenapyr; nicotinic acetylcholine receptor (nAChR) channel blockers such as the nereistoxin analogs cartap; inhibitors of chitin biosynthesis such as the benzoylureas flufenoxuron, hexaflumuron, lufenuron, novaluron, noviflumuron and triflumuron, and buprofezin; dipteran moulting disrupters such as cyromazine; ecdysone receptor agonists such as the diacylhydrazines methoxyfenozide and tebufenozide; octopamine receptor agonists such as amitraz; mitochondrial complex III electron transport inhibitors such as hydramethylnon; mitochondrial complex I electron transport inhibitors such as pyridaben; voltage-dependent sodium channel blockers such as indoxacarb; inhibitors of acetyl CoA carboxylase such as the tetronic and tetramic acids spirodiclofen, spiromesifen and spirotetramat; mitochondrial complex II electron transport inhibitors such as the β-ketonitriles cyenopyrafen and cyflumetofen; ryanidine receptor modulators such as the anthranilic diamides chlorantraniliprole, cyantraniliprole and cyantraniliprole, diamides such as flubendiamide, and ryanodine receptor ligands such as ryanodine; compounds wherein the target site responsible for biological activity is unknown or uncharacterized such as azadirachtin, bifenazate, pyridalyl, pyrifluquinazon and triflumezopyrim; microbial disrupters of insect midgut membranes such as *Bacillus thuringensis* and the delta-endotoxins they produce and *Bacillus sphaericus*; and biological agents including nucleo polyhedro viruses (NPV) and other naturally occurring or genetically modified insecticidal viruses.

Further examples of biologically active compounds or agents with which compounds of this invention can be formulated are: fungicides such as acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpropidin, fenpropimorph, fenpyrazamine, fentin acetate, fentin hydroxide, ferbam, ferimzone, flometoquin, fluazinam, fludioxonil, flufenoxystrobin, flumorph, fluopicolide, fluopyram, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, iodicarb, ipconazole, isofetamid, iprobenfos, iprodione, iprovalicarb, isoprothiolane, isopyrazam, isotianil, kasugamycin, kresoxim-methyl, mancozeb, mandipropamid, mandestrobin, maneb, mapanipyrin, mepronil, meptyldinocap, metalaxyl (including metalaxyl-M/mefenoxam), metconazole, methasulfocarb, metiram, metominostrobin, metrafenone, myclobutanil, naftitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetyl-aluminm), picoxystrobin, piperalin, polyoxin, probenazole, prochloraz, procymidone, propamocarb, propiconazole, propineb, proquinazid, prothiocarb, prothioconazole, pyraclostrobin, pyrametostrobin, pyraoxystrobin, pyrazophos, pyribencarb, pyributacarb, pyrifenox, pyriofenone, perisoxazole, pyrimethanil, pyrifenox, pyrrolnitrin, pyroquilon, quinconazole, quinmethionate, quinoxyfen, quintozene, silthiofam, sedaxane, simeconazole, spiroxamine, streptomycin, sulfur, tebuconazole, tebufloquin, tecloſthalam, tecloſtalam, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, trifloxystrobin, triforine, triticonazole, uniconazole, validamycin, valifenalate (also known as valifenal), vinclozolin, zineb, ziram, zoxamide and 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H- pyrazol-1-yl]ethanone; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, *Bacillus firmus* and *Pasteuria nishizawae*; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, $2^{nd}$ Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a compound of Formula 1 (e.g., "50:1 to 1:50" of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
|---|---|---|
| Abamectin | chloride channel activator | 50:1 to 1:50 |
| Acetamiprid | nicotinic acetylcholinereceptor (nAChR) agonist | 150:1 to 1:200 |
| Amitraz | octopamine receptor agonists | 200:1 to 1:100 |
| Avermectin | macrocyclic lactones | 50:1 to 1:50 |
| Azadirachtin | unknown site of action | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin biosynthesis inhibitors | 500:1 to 1:50 |
| Cartap | nicotinic acetylcholine receptor (nAChR) channel blocker | 100:1 to 1:200 |
| Chlorantraniliprole | ryanodine receptor modulator | 100:1 to 1:120 |
| Chlorfenapyr | uncouplers of oxidative phosphorylation | 300:1 to 1:200 |
| Chlorpyrifos | acetylcholinesterase inhibitor | 500:1 to 1:200 |
| Clothianidin | nicotinic acetylcholine receptor (nAChR) agonist | 100:1 to 1:400 |
| Cyantraniliprole | Ryanodine receptor modulator | 100:1 to 1:120 |
| Cyfluthrin | sodium channel modulator | 150:1 to 1:200 |
| Cyhalothrin | sodium channel modulator | 150:1 to 1:200 |
| Cypermethrin | sodium channel modulator | 150:1 to 1:200 |
| Cyromazine | dipteran moulting disrupter | 400:1 to 1:50 |
| Deltamethrin | sodium channel modulators | 50:1 to 1:400 |
| Dieldrin | GABA-gated chloride channel antagonist | 200:1 to 1:100 |
| Dinotefuran | nicotinic acetylcholine receptor (nAChR) agonist | 150:1 to 1:200 |
| Diofenolan | juvenile hormone mimic | 150:1 to 1:200 |
| Emamectin | chloride channel activator | 50:1 to 1:10 |
| Endosulfan | GABA-gated chloride channel antagonist | 200:1 to 1:100 |
| Esfenvalerate | sodium channel modulator | 100:1 to 1:400 |
| Ethiprole | GABA-regulated chloride channel antagonist | 200:1 to 1:100 |
| Fenothiocarb | | 150:1 to 1:200 |
| Fenoxycarb | juvenile hormone mimic | 500:1 to 1:100 |
| Fenvalerate | sodium channel modulator | 150:1 to 1:200 |
| Fipronil | GABA-regulated chloride channel antagonist | 150:1 to 1:100 |
| Flonicamid | selective homopteran feeding blocker | 200:1 to 1:100 |
| Flubendiamide | ryanodine receptor modulator | 100:1 to 1:120 |
| Flufenoxuron | chitin biosynthesis inhibitor | 200:1 to 1:100 |
| Hexaflumuron | chitin biosynthesis inhibitor | 300:1 to 1:50 |
| Hydramethylnon | mitochondrial Complex III electron transport inhibitors | 150:1 to 1:250 |
| Imidacloprid | nicotinic acetylcholine receptor (nAChR) agonist | 1000:1 to 1:1000 |
| Indoxacarb | voltage-dependent sodium channel blocker | 200:1 to 1:50 |
| Lambda-cyhalothrin | sodium channel modulator | 50:1 to 1:250 |
| Lufenuron | chitin biosynthesis inhibitor | 500:1 to 1:250 |
| Metaflumizone | voltage-dependent sodium channel blocker | 200:1 to 1:200 |
| Methomyl | acetylcholinesterase inhibitor | 500:1 to 1:100 |
| Methoprene | juvenile hormone mimic | 500:1 to 1:100 |
| Methoxyfenozide | ecdysone receptor agonist | 50:1 to 1:50 |
| Nitenpyram | nicotinic acetylcholine receptor (nAChR) agonist | 150:1 to 1:200 |
| Nithiazine | nicotinic acetylcholine receptor (nAChR) agonist | 150:1 to 1:200 |
| Novaluron | chitin biosynthesis inhibitor | 500:1 to 1:150 |
| Oxamyl | acetylcholinesterase inhibitors | 200:1 to 1:200 |
| Pymetrozine | selective homopteran feeding blocker | 200:1 to 1:100 |
| Pyrethrin | sodium channel modulator | 100:1 to 1:10 |
| Pyridaben | mitochondrial Complex I electron transport inhibitor | 200:1 to 1:100 |

TABLE A-continued

| Invertebrate Pest Control Agent | Mode of Action or Chemical Class | Typical Weight Ratio |
|---|---|---|
| Pyridalyl | unknown site of action | 200:1 to 1:100 |
| Pyriproxyfen | juvenile hormone mimic | 500:1 to 1:100 |
| Ryanodine | ryanodine receptor ligand | 100:1 to 1:120 |
| Spinetoram | nicotinic acetylcholine receptor (nAChR) allosteric activator | 150:1 to 1:100 |
| Spinosad | nicotinic acetylcholine receptor (nAChR) allosteric activators | 500:1 to 1:10 |
| Spirodiclofen | acetyl CoA carboxylase inhibitor | 200:1 to 1:200 |
| Spiromesifen | acetyl CoA carboxylase inhibitor | 200:1 to 1:200 |
| Tebufenozide | ecdysone receptor agonist | 500:1 to 1:250 |
| Thiacloprid | nicotinic acetylcholine receptor (nAChR) agonist | 100:1 to 1:200 |
| Thiamethoxam | nicotinic acetylcholine receptor (nAChR) agonist | 1250:1 to 1:1000 |
| Thiodicarb | acetylcholinesterase inhibitors | 500:1 to 1:400 |
| Thiosultap-sodium | Nicotinic acetylcholine receptor (nAChR) channel blocker | 150:1 to 1:100 |
| Tralomethrin | sodium channel modulator | 150:1 to 1:200 |
| Triazamate | acetyl cholinesterase inhibitors | 250:1 to 1:100 |
| Triflumezopyrim | | |
| Triflumuron | chitin synthesis inhibitor | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the Invertebrate Pest Control Agents listed in Table A above.

The weight ratios of a compound, including a compound of Formula 1, an N-oxide or a salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Tables B1 to B9 are embodiments of specific compositions comprising a compound of Formula 1 (compound numbers refer to compounds in Index Tables A-B) and an additional invertebrate pest control agent.

TABLE B1

| Mixture No. | Cmpd. No. | and | Invertebrate Pest Control Agent |
|---|---|---|---|
| B1-1 | 14 | and | Abamectin |
| B1-2 | 14 | and | Acetamiprid |
| B1-3 | 14 | and | Amitraz |
| B1-4 | 14 | and | Avermectin |
| B1-5 | 14 | and | Azadirachtin |
| B1-6 | 14 | and | Bensultap |
| B1-7 | 14 | and | Beta-cyfluthrin |
| B1-8 | 14 | and | Bifenthrin |
| B1-9 | 14 | and | Buprofezin |
| B1-10 | 14 | and | Cartap |
| B1-11 | 14 | and | Chlorantraniliprole |
| B1-12 | 14 | and | Chlorfenapyr |
| B1-13 | 14 | and | Chlorpyrifos |
| B1-14 | 14 | and | Clothianidin |
| B1-15 | 14 | and | Cyantraniliprole |
| B1-16 | 14 | and | Cyfluthrin |
| B1-17 | 14 | and | Cyhalothrin |
| B1-18 | 14 | and | Cypermethrin |
| B1-19 | 14 | and | Cyromazine |
| B1-20 | 14 | and | Deltamethrin |
| B1-21 | 14 | and | Dieldrin |
| B1-22 | 14 | and | Dinotefuran |
| B1-23 | 14 | and | Diofenolan |
| B1-24 | 14 | and | Emamectin |
| B1-25 | 14 | and | Endosulfan |
| B1-26 | 14 | and | Esfenvalerate |
| B1-27 | 14 | and | Ethiprole |
| B1-28 | 14 | and | Fenothiocarb |
| B1-29 | 14 | and | Fenoxycarb |
| B1-30 | 14 | and | Fenvalerate |
| B1-31 | 14 | and | Fipronil |
| B1-32 | 14 | and | Flonicamid |
| B1-33 | 14 | and | Flubendiamide |
| B1-34 | 14 | and | Flufenoxuron |
| B1-35 | 14 | and | Hexaflumuron |
| B1-36 | 14 | and | Hydramethylnon |
| B1-37 | 14 | and | Imidacloprid |
| B1-38 | 14 | and | Indoxacarb |
| B1-39 | 14 | and | Lambda-cyhalothrin |
| B1-40 | 14 | and | Lufenuron |
| B1-41 | 14 | and | Metaflumizone |
| B1-42 | 14 | and | Methomyl |
| B1-43 | 14 | and | Methoprene |
| B1-44 | 14 | and | Methoxyfenozide |
| B1-45 | 14 | and | Nitenpyram |
| B1-46 | 14 | and | Nithiazine |
| B1-47 | 14 | and | Novaluron |
| B1-48 | 14 | and | Oxamyl |
| B1-49 | 14 | and | Phosmet |
| B1-50 | 14 | and | Pymetrozine |
| B1-51 | 14 | and | Pyrethrin |
| B1-52 | 14 | and | Pyridaben |
| B1-53 | 14 | and | Pyridalyl |
| B1-54 | 14 | and | Pyriproxyfen |
| B1-55 | 14 | and | Ryanodine |
| B1-56 | 14 | and | Spinetoram |
| B1-57 | 14 | and | Spinosad |
| B1-58 | 14 | and | Spirodiclofen |
| B1-59 | 14 | and | Spiromesifen |
| B1-60 | 14 | and | Spirotetramat |
| B1-61 | 14 | and | Sulfoxaflor |
| B1-62 | 14 | and | Tebufenozide |
| B1-63 | 14 | and | Tefluthrin |
| B1-64 | 14 | and | Thiacloprid |
| B1-65 | 14 | and | Thiamethoxam |
| B1-66 | 14 | and | Thiodicarb |
| B1-67 | 14 | and | Thiosultap-sodium |
| B1-68 | 14 | and | Tolfenpyrad |
| B1-69 | 14 | and | Tralomethrin |
| B1-70 | 14 | and | Triazamate |
| B1-71 | 14 | and | Triflumezopyrim |
| B1-72 | 14 | and | Triflumuron |
| B1-73 | 14 | and | *Bacillus thuringiensis* |
| B1-74 | 14 | and | *Bacillus thuringiensis* delta-endotoxin |
| B1-75 | 14 | and | NPV (e.g., Gemstar) |

Table B2

Table 2 is identical to Table B1, except that each reference to compound 14 in the column headed "Cmpd. No." is replaced by a reference to compound 15. For example, the first mixture in Table B2 is designated B2-1 and is a mixture of compound 15 and the additional invertebrate pest control agent abamectin.

Table B3

Table B3 is identical to Table B1, except that each reference to compound 14 in the column headed "Cmpd. No." is replaced by a reference to compound 20. For example, the first mixture in Table B3 is designated B3-1 and is a mixture of compound 20 and the additional invertebrate pest control agent abamectin.

Table B4

Table B4 is identical to Table B1, except that each reference to compound 14 in the column headed "Cmpd. No." is replaced by a reference to compound 22. For example, the first mixture in Table B4 is designated B4-1 and is a mixture of compound 22 and the additional invertebrate pest control agent abamectin.

Table B5

Table B5 is identical to Table B1, except that each reference to compound 14 in the column headed "Cmpd. No." is replaced by a reference to compound 23. For example, the first mixture in Table B5 is designated B5-1 and is a mixture of compound 23 and the additional invertebrate pest control agent abamectin.

Table B6

Table B6 is identical to Table B1, except that each reference to compound 14 in the column headed "Cmpd. No." is replaced by a reference to compound 47. For example, the first mixture in Table B6 is designated B6-1 and is a mixture of compound 47 and the additional invertebrate pest control agent abamectin.

Table B7

Table B7 is identical to Table B1, except that each reference to compound 14 in the column headed "Cmpd. No." is replaced by a reference to compound 48. For example, the first mixture in Table B7 is designated B7-1 and is a mixture of compound 48 and the additional invertebrate pest control agent abamectin.

Table B8

Table B8 is identical to Table B1, except that each reference to compound 14 in the column headed "Cmpd. No." is replaced by a reference to compound 51. For example, the first mixture in Table B8 is designated B8-1 and is a mixture of compound 51 and the additional invertebrate pest control agent abamectin.

Table B9

Table B9 is identical to Table B1, except that each reference to compound 14 in the column headed "Cmpd. No." is replaced by a reference to compound 54. For example, the first mixture in Table B9 is designated B9-1 and is a mixture of compound 54 and the additional invertebrate pest control agent abamectin.

The specific mixtures listed in Tables B1 to B9 typically combine a compound of Formula 1 with the other invertebrate pest agent in the ratios specified in Table A.

Listed below in Tables C1 to C9 are specific mixtures comprising a compound of Formula 1 (compound numbers (Cmpd. No.) refer to compounds in Index Tables A-B) and an additional invertebrate pest control agent. Tables C1 to C9 further list specific weight ratios typical of the mixtures of Tables C1 to C9. For example, the first weight ratio entry of the first line of Table C1 specifically discloses the mixture of Compound 14 of Index Table A with abamectin applied in a weight ratio of 100 parts Compound 14 to 1 part abamectin.

TABLE C1

| Mixture No. | Cmpd. No. | and | Invertebrate Pest Control Agent | Typical Mixture Ratios (by weight) | | | | | | | |
|---|---|---|---|---|---|---|---|---|---|---|---|
| C1-1 | 14 | and | Abamectin | 100:1 | 10:1 | 5:1 | 2:1 | 1:1 | 1:2 | 1:5 | 1:10 | 1:100 |
| C1-2 | 14 | and | Acetamiprid | 100:1 | 10:1 | 5:1 | 2:1 | 1:1 | 1:2 | 1:5 | 1:10 | 1:100 |
| C1-3 | 14 | and | Amitraz | 100:1 | 10:1 | 5:1 | 2:1 | 1:1 | 1:2 | 1:5 | 1:10 | 1:100 |
| C1-4 | 14 | and | Avermectin | 100:1 | 10:1 | 5:1 | 2:1 | 1:1 | 1:2 | 1:5 | 1:10 | 1:100 |
| C1-5 | 14 | and | Azadirachtin | 100:1 | 10:1 | 5:1 | 2:1 | 1:1 | 1:2 | 1:5 | 1:10 | 1:100 |
| C1-6 | 14 | and | Bensultap | 100:1 | 10:1 | 5:1 | 2:1 | 1:1 | 1:2 | 1:5 | 1:10 | 1:100 |
| C1-7 | 14 | and | Beta-cyfluthrin | 100:1 | 10:1 | 5:1 | 2:1 | 1:1 | 1:2 | 1:5 | 1:10 | 1:100 |
| C1-8 | 14 | and | Bifenthrin | 100:1 | 10:1 | 5:1 | 2:1 | 1:1 | 1:2 | 1:5 | 1:10 | 1:100 |
| C1-9 | 14 | and | Buprofezin | 100:1 | 10:1 | 5:1 | 2:1 | 1:1 | 1:2 | 1:5 | 1:10 | 1:100 |
| C1-10 | 14 | and | Cartap | 100:1 | 10:1 | 5:1 | 2:1 | 1:1 | 1:2 | 1:5 | 1:10 | 1:100 |
| C1-11 | 14 | and | Chlorantraniliprole | 100:1 | 10:1 | 5:1 | 2:1 | 1:1 | 1:2 | 1:5 | 1:10 | 1:100 |
| C1-12 | 14 | and | Chlorfenapyr | 100:1 | 10:1 | 5:1 | 2:1 | 1:1 | 1:2 | 1:5 | 1:10 | 1:100 |
| C1-13 | 14 | and | Chlorpyrifos | 100:1 | 10:1 | 5:1 | 2:1 | 1:1 | 1:2 | 1:5 | 1:10 | 1:100 |
| C1-14 | 14 | and | Clothianidin | 100:1 | 10:1 | 5:1 | 2:1 | 1:1 | 1:2 | 1:5 | 1:10 | 1:100 |
| C1-15 | 14 | and | Cyantraniliprole | 100:1 | 10:1 | 5:1 | 2:1 | 1:1 | 1:2 | 1:5 | 1:10 | 1:100 |
| C1-16 | 14 | and | Cyfluthrin | 100:1 | 10:1 | 5:1 | 2:1 | 1:1 | 1:2 | 1:5 | 1:10 | 1:100 |
| C1-17 | 14 | and | Cyhalothrin | 100:1 | 10:1 | 5:1 | 2:1 | 1:1 | 1:2 | 1:5 | 1:10 | 1:100 |
| C1-18 | 14 | and | Cypermethrin | 100:1 | 10:1 | 5:1 | 2:1 | 1:1 | 1:2 | 1:5 | 1:10 | 1:100 |
| C1-19 | 14 | and | Cyromazine | 100:1 | 10:1 | 5:1 | 2:1 | 1:1 | 1:2 | 1:5 | 1:10 | 1:100 |
| C1-20 | 14 | and | Deltamethrin | 100:1 | 10:1 | 5:1 | 2:1 | 1:1 | 1:2 | 1:5 | 1:10 | 1:100 |
| C1-21 | 14 | and | Dieldrin | 100:1 | 10:1 | 5:1 | 2:1 | 1:1 | 1:2 | 1:5 | 1:10 | 1:100 |
| C1-22 | 14 | and | Dinotefuran | 100:1 | 10:1 | 5:1 | 2:1 | 1:1 | 1:2 | 1:5 | 1:10 | 1:100 |
| C1-23 | 14 | and | Diofenolan | 100:1 | 10:1 | 5:1 | 2:1 | 1:1 | 1:2 | 1:5 | 1:10 | 1:100 |
| C1-24 | 14 | and | Emamectin | 100:1 | 10:1 | 5:1 | 2:1 | 1:1 | 1:2 | 1:5 | 1:10 | 1:100 |
| C1-25 | 14 | and | Endosulfan | 100:1 | 10:1 | 5:1 | 2:1 | 1:1 | 1:2 | 1:5 | 1:10 | 1:100 |
| C1-26 | 14 | and | Esfenvalerate | 100:1 | 10:1 | 5:1 | 2:1 | 1:1 | 1:2 | 1:5 | 1:10 | 1:100 |
| C1-27 | 14 | and | Ethiprole | 100:1 | 10:1 | 5:1 | 2:1 | 1:1 | 1:2 | 1:5 | 1:10 | 1:100 |
| C1-28 | 14 | and | Fenothiocarb | 100:1 | 10:1 | 5:1 | 2:1 | 1:1 | 1:2 | 1:5 | 1:10 | 1:100 |
| C1-29 | 14 | and | Fenoxycarb | 100:1 | 10:1 | 5:1 | 2:1 | 1:1 | 1:2 | 1:5 | 1:10 | 1:100 |
| C1-30 | 14 | and | Fenvalerate | 100:1 | 10:1 | 5:1 | 2:1 | 1:1 | 1:2 | 1:5 | 1:10 | 1:100 |
| C1-31 | 14 | and | Fipronil | 100:1 | 10:1 | 5:1 | 2:1 | 1:1 | 1:2 | 1:5 | 1:10 | 1:100 |
| C1-32 | 14 | and | Flonicamid | 100:1 | 10:1 | 5:1 | 2:1 | 1:1 | 1:2 | 1:5 | 1:10 | 1:100 |
| C1-33 | 14 | and | Flubendiamide | 100:1 | 10:1 | 5:1 | 2:1 | 1:1 | 1:2 | 1:5 | 1:10 | 1:100 |
| C1-34 | 14 | and | Flufenoxuron | 100:1 | 10:1 | 5:1 | 2:1 | 1:1 | 1:2 | 1:5 | 1:10 | 1:100 |
| C1-35 | 14 | and | Hexaflumuron | 100:1 | 10:1 | 5:1 | 2:1 | 1:1 | 1:2 | 1:5 | 1:10 | 1:100 |

TABLE C1-continued

| Mixture No. | Cmpd. No. | and | Invertebrate Pest Control Agent | Typical Mixture Ratios (by weight) | | | | | | | | |
|---|---|---|---|---|---|---|---|---|---|---|---|---|
| C1-36 | 14 | and | Hydramethylnon | 100:1 | 10:1 | 5:1 | 2:1 | 1:1 | 1:2 | 1:5 | 1:10 | 1:100 |
| C1-37 | 14 | and | Imidacloprid | 100:1 | 10:1 | 5:1 | 2:1 | 1:1 | 1:2 | 1:5 | 1:10 | 1:100 |
| C1-38 | 14 | and | Indoxacarb | 100:1 | 10:1 | 5:1 | 2:1 | 1:1 | 1:2 | 1:5 | 1:10 | 1:100 |
| C1-39 | 14 | and | Lambda-cyhalothrin | 100:1 | 10:1 | 5:1 | 2:1 | 1:1 | 1:2 | 1:5 | 1:10 | 1:100 |
| C1-40 | 14 | and | Lufenuron | 100:1 | 10:1 | 5:1 | 2:1 | 1:1 | 1:2 | 1:5 | 1:10 | 1:100 |
| C1-41 | 14 | and | Metaflumizone | 100:1 | 10:1 | 5:1 | 2:1 | 1:1 | 1:2 | 1:5 | 1:10 | 1:100 |
| C1-42 | 14 | and | Methomyl | 100:1 | 10:1 | 5:1 | 2:1 | 1:1 | 1:2 | 1:5 | 1:10 | 1:100 |
| C1-43 | 14 | and | Methoprene | 100:1 | 10:1 | 5:1 | 2:1 | 1:1 | 1:2 | 1:5 | 1:10 | 1:100 |
| C1-44 | 14 | and | Methoxyfenozide | 100:1 | 10:1 | 5:1 | 2:1 | 1:1 | 1:2 | 1:5 | 1:10 | 1:100 |
| C1-45 | 14 | and | Nitenpyram | 100:1 | 10:1 | 5:1 | 2:1 | 1:1 | 1:2 | 1:5 | 1:10 | 1:100 |
| C1-46 | 14 | and | Nithiazine | 100:1 | 10:1 | 5:1 | 2:1 | 1:1 | 1:2 | 1:5 | 1:10 | 1:100 |
| C1-47 | 14 | and | Novaluron | 100:1 | 10:1 | 5:1 | 2:1 | 1:1 | 1:2 | 1:5 | 1:10 | 1:100 |
| C1-48 | 14 | and | Oxamyl | 100:1 | 10:1 | 5:1 | 2:1 | 1:1 | 1:2 | 1:5 | 1:10 | 1:100 |
| C1-49 | 14 | and | Phosmet | 100:1 | 10:1 | 5:1 | 2:1 | 1:1 | 1:2 | 1:5 | 1:10 | 1:100 |
| C1-50 | 14 | and | Pymetrozine | 100:1 | 10:1 | 5:1 | 2:1 | 1:1 | 1:2 | 1:5 | 1:10 | 1:100 |
| C1-51 | 14 | and | Pyrethrin | 100:1 | 10:1 | 5:1 | 2:1 | 1:1 | 1:2 | 1:5 | 1:10 | 1:100 |
| C1-52 | 14 | and | Pyridaben | 100:1 | 10:1 | 5:1 | 2:1 | 1:1 | 1:2 | 1:5 | 1:10 | 1:100 |
| C1-53 | 14 | and | Pyridalyl | 100:1 | 10:1 | 5:1 | 2:1 | 1:1 | 1:2 | 1:5 | 1:10 | 1:100 |
| C1-54 | 14 | and | Pyriproxyfen | 100:1 | 10:1 | 5:1 | 2:1 | 1:1 | 1:2 | 1:5 | 1:10 | 1:100 |
| C1-55 | 14 | and | Ryanodine | 100:1 | 10:1 | 5:1 | 2:1 | 1:1 | 1:2 | 1:5 | 1:10 | 1:100 |
| C1-56 | 14 | and | Spinetoram | 100:1 | 10:1 | 5:1 | 2:1 | 1:1 | 1:2 | 1:5 | 1:10 | 1:100 |
| C1-57 | 14 | and | Spinosad | 100:1 | 10:1 | 5:1 | 2:1 | 1:1 | 1:2 | 1:5 | 1:10 | 1:100 |
| C1-58 | 14 | and | Spirodiclofen | 100:1 | 10:1 | 5:1 | 2:1 | 1:1 | 1:2 | 1:5 | 1:10 | 1:100 |
| C1-59 | 14 | and | Spiromesifen | 100:1 | 10:1 | 5:1 | 2:1 | 1:1 | 1:2 | 1:5 | 1:10 | 1:100 |
| C1-60 | 14 | and | Spirotetramat | 100:1 | 10:1 | 5:1 | 2:1 | 1:1 | 1:2 | 1:5 | 1:10 | 1:100 |
| C1-61 | 14 | and | Sulfoxaflor | 100:1 | 10:1 | 5:1 | 2:1 | 1:1 | 1:2 | 1:5 | 1:10 | 1:100 |
| C1-62 | 14 | and | Tebufenozide | 100:1 | 10:1 | 5:1 | 2:1 | 1:1 | 1:2 | 1:5 | 1:10 | 1:100 |
| C1-63 | 14 | and | Tefluthrin | 100:1 | 10:1 | 5:1 | 2:1 | 1:1 | 1:2 | 1:5 | 1:10 | 1:100 |
| C1-64 | 14 | and | Thiacloprid | 100:1 | 10:1 | 5:1 | 2:1 | 1:1 | 1:2 | 1:5 | 1:10 | 1:100 |
| C1-65 | 14 | and | Thiamethoxam | 100:1 | 10:1 | 5:1 | 2:1 | 1:1 | 1:2 | 1:5 | 1:10 | 1:100 |
| C1-66 | 14 | and | Thiodicarb | 100:1 | 10:1 | 5:1 | 2:1 | 1:1 | 1:2 | 1:5 | 1:10 | 1:100 |
| C1-67 | 14 | and | Thiosultap-sodium | 100:1 | 10:1 | 5:1 | 2:1 | 1:1 | 1:2 | 1:5 | 1:10 | 1:100 |
| C1-68 | 14 | and | Tolfenpyrad | 100:1 | 10:1 | 5:1 | 2:1 | 1:1 | 1:2 | 1:5 | 1:10 | 1:100 |
| C1-69 | 14 | and | Tralomethrin | 100:1 | 10:1 | 5:1 | 2:1 | 1:1 | 1:2 | 1:5 | 1:10 | 1:100 |
| C1-70 | 14 | and | Triazamate | 100:1 | 10:1 | 5:1 | 2:1 | 1:1 | 1:2 | 1:5 | 1:10 | 1:100 |
| C1-71 | 14 | and | Triflumezopyrim | 100:1 | 10:1 | 5:1 | 2:1 | 1:1 | 1:2 | 1:5 | 1:10 | 1:100 |
| C1-72 | 14 | and | Triflumuron | 100:1 | 10:1 | 5:1 | 2:1 | 1:1 | 1:2 | 1:5 | 1:10 | 1:100 |
| C1-73 | 14 | and | *Bacillus thuringiensis* | 100:1 | 10:1 | 5:1 | 2:1 | 1:1 | 1:2 | 1:5 | 1:10 | 1:100 |
| C1-74 | 14 | and | *Bacillus thuringiensis* delta-endotoxin | 100:1 | 10:1 | 5:1 | 2:1 | 1:1 | 1:2 | 1:5 | 1:10 | 1:100 |
| C1-75 | 14 | and | NPV (e.g., Gemstar) | 100:1 | 10:1 | 5:1 | 2:1 | 1:1 | 1:2 | 1:5 | 1:10 | 1:100 |

Table C2

Table C2 is identical to Table C1, except that each reference to compound 14 in the column headed "Cmpd. No." is replaced by a reference to compound 15. For example, the first weight ratio entry of the first line of Table C2 specifically discloses the mixture of Compound 15 with abamectin applied in a weight ratio of 100 parts Compound 15 to 1 part abamectin.

Table C3

Table C3 is identical to Table C1, except that each reference to compound 14 in the column headed "Cmpd. No." is replaced by a reference to compound 20. For example, the first weight ratio entry of the first line of Table C3 specifically discloses the mixture of Compound 20 with abamectin applied in a weight ratio of 100 parts Compound 20 to 1 part abamectin.

Table C4

Table C4 is identical to Table C1, except that each reference to compound 14 in the column headed "Cmpd. No." is replaced by a reference to compound 22. For example, the first weight ratio entry of the first line of Table C4 specifically discloses the mixture of Compound 22 with abamectin applied in a weight ratio of 100 parts Compound 22 to 1 part abamectin.

Table C5

Table C5 is identical to Table C1, except that each reference to compound 14 in the column headed "Cmpd. No." is replaced by a reference to compound 23. For example, the first weight ratio entry of the first line of Table C5 specifically discloses the mixture of Compound 23 with abamectin applied in a weight ratio of 100 parts Compound 23 to 1 part abamectin.

Table C6

Table C6 is identical to Table C1, except that each reference to compound 14 in the column headed "Cmpd. No." is replaced by a reference to compound 47. For example, the first weight ratio entry of the first line of Table C6 specifically discloses the mixture of Compound 47 with abamectin applied in a weight ratio of 100 parts Compound 47 to 1 part abamectin.

Table C7

Table C7 is identical to Table C1, except that each reference to compound 14 in the column headed "Cmpd. No." is replaced by a reference to compound 48. For example, the first weight ratio entry of the first line of Table C7 specifically discloses the mixture of Compound 48 with abamectin applied in a weight ratio of 100 parts Compound 48 to 1 part abamectin.

Table C8

Table C8 is identical to Table C1, except that each reference to compound 14 in the column headed "Cmpd. No." is replaced by a reference to compound 51. For example, the first weight ratio entry of the first line of Table C8 specifically discloses the mixture of Compound 51 with abamectin applied in a weight ratio of 100 parts Compound 51 to 1 part abamectin.

Table C9

Table C9 is identical to Table C1, except that each reference to compound 14 in the column headed "Cmpd. No." is replaced by a reference to compound 54. For example, the first weight ratio entry of the first line of Table C9 specifically discloses the mixture of Compound 54 with abamectin applied in a weight ratio of 100 parts Compound 54 to 1 part abamectin.

Listed below in Tables D1 to D9 are embodiments of specific compositions comprising a compound of Formula 1 (compound numbers (Cmpd. No.) refer to compounds in Index Tables A-B) and an additional fungicide.

TABLE D1

| Mixture No. | Cmpd. No. | and | Fungicide |
|---|---|---|---|
| D1-1 | 3 | and | Probenazole |
| D1-2 | 3 | and | Tiadinil |
| D1-3 | 3 | and | Isotianil |
| D1-4 | 3 | and | Pyroquilon |
| D1-5 | 14 | and | Metominostrobin |
| D1-6 | 14 | and | Flutolanil |
| D1-7 | 14 | and | Validamycin |
| D1-8 | 14 | and | Furametpyr |
| D1-9 | 14 | and | Pencycuron |
| D1-10 | 14 | and | Simeconazole |
| D1-11 | 14 | and | Orysastrobin |
| D1-12 | 14 | and | Trifloxystrobin |
| D1-13 | 14 | and | Isoprothiolane |
| D1-14 | 14 | and | Azoxystrobin |
| D1-15 | 14 | and | Tricyclazole |
| D1-16 | 14 | and | Hexaconazole |
| D1-17 | 3 | and | Difenoconazole |
| D1-18 | 3 | and | Cyproconazole |
| D1-19 | 3 | and | Propiconazole |
| D1-20 | 3 | and | Fenoxanil |
| D1-21 | 14 | and | Ferimzone |
| D1-22 | 14 | and | Fthalide |
| D1-23 | 14 | and | Kasugamycin |
| D1-24 | 14 | and | Picoxystrobin |
| D1-25 | 14 | and | Penthiopyrad |
| D1-26 | 14 | and | Famoxadone |
| D1-27 | 14 | and | Cymoxanil |
| D1-28 | 14 | and | Proquinazid |
| D1-29 | 14 | and | Flusilazole |
| D1-30 | 14 | and | Mancozeb |
| D1-31 | 14 | and | Copper hydroxide |
| D1-32 | 14 | and | Oxathiapiprolin |

Table D2

Table D2 is identical to Table D1, except that each reference to compound 14 in the column headed "Cmpd. No." is replaced by a reference to compound 15. For example, the first mixture in Table D2 is designated D2-1 and is a mixture of compound 15 and the additional fungicide probenazole.

Table D3

Table D3 is identical to Table D1, except that each reference to compound 14 in the column headed "Cmpd. No." is replaced by a reference to compound 20. For example, the first mixture in Table D3 is designated D3-1 and is a mixture of compound 20 and the additional fungicide probenazole.

Table D4

Table D4 is identical to Table D1, except that each reference to compound 14 in the column headed "Cmpd. No." is replaced by a reference to compound 22. For example, the first mixture in Table D4 is designated D4-1 and is a mixture of compound 22 and the additional fungicide probenazole.

Table D5

Table D5 is identical to Table D1, except that each reference to compound 14 in the column headed "Cmpd. No." is replaced by a reference to compound 23. For example, the first mixture in Table D5 is designated D5-1 and is a mixture of compound 23 and the additional fungicide probenazole.

Table D6

Table D6 is identical to Table D1, except that each reference to compound 14 in the column headed "Cmpd. No." is replaced by a reference to compound 47. For example, the first mixture in Table D6 is designated D6-1 and is a mixture of compound 47 and the additional fungicide probenazole.

Table D7

Table D7 is identical to Table D1, except that each reference to compound 14 in the column headed "Cmpd. No." is replaced by a reference to compound 48. For example, the first mixture in Table D7 is designated D7-1 and is a mixture of compound 48 and the additional fungicide probenazole.

Table D8

Table D8 is identical to Table D1, except that each reference to compound 14 in the column headed "Cmpd. No." is replaced by a reference to compound 51. For example, the first mixture in Table D8 is designated D8-1 and is a mixture of compound 51 and the additional fungicide probenazole.

Table D9

Table D9 is identical to Table D1, except that each reference to compound 14 in the column headed "Cmpd.

No." is replaced by a reference to compound 54. For example, the first mixture in Table D9 is designated D9-1 and is a mixture of compound 54 and the additional fungicide probenazole.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of the invention are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant and seed cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants and seeds can be genetically modified to exhibit traits of, for example, herbicide tolerance, insect-resistance, modified oil profiles or drought tolerance. Useful genetically modified plants and seeds containing single gene transformation events or combinations of transformation events are listed in Table Z. Additional information for the genetic modifications listed in Table Z can be obtained from the following databases:

http://www2.oecd.org/biotech/byidentifier.aspx
http://www.aphis.usda.go
http://gmoinfo.jrc.ec.europa.eu The following abbreviations are used in Table Z which follows: tol. is tolerance, res. is resistance, SU is sulfonylurea, ALS is acetolactate synthase, HPPD is 4-Hydroxyphenylpyruvate Dioxygenase, NA is Not Available?

TABLE Z

| Crop | Event Name | Event Code | Trait(s) | Gene(s) |
|---|---|---|---|---|
| Alfalfa | J101 | MON-00101-8 | Glyphosate tol. | cp4 epsps (aroA: CP4) |
| Alfalfa | J163 | MON-ØØ163-7 | Glyphosate tol. | cp4 epsps (aroA: CP4) |
| Canola* | 23-18-17 (Event 18) | CGN-89465-2 | High lauric acid oil | te |
| Canola* | 23-198 (Event 23) | CGN-89465-2 | High lauric acid oil | te |
| Canola* | 61061 | DP-Ø61Ø61-7 | Glyphosate tol. | gat4621 |
| Canola* | 73496 | DP-Ø73496-4 | Glyphosate tol. | gat4621 |
| Canola* | GT200 (RT200) | MON-89249-2 | Glyphosate tol. | cp4 epsps (aroA: CP4); goxv247 |
| Canola* | GT73 (RT73) | MON-ØØØ73-7 | Glyphosate tol. | cp4 epsps (aroA: CP4); goxv247 |
| Canola* | HCN10 (Topas 19/2) | NA | Glufosinate tol. | bar |
| Canola* | HCN28 (T45) | ACS-BNØØ8-2 | Glufosinate tol. | pat (syn) |
| Canola* | HCN92 (Topas 19/2) | ACS-BNØØ7-1 | Glufosinate tol. | bar |
| Canola* | MON88302 | MON-883Ø2-9 | Glyphosate tol. | cp4 epsps (aroA: CP4) |
| Canola* | MPS961 | NA | Phytate breakdown | phyA |
| Canola* | MPS962 | NA | Phytate breakdown | phyA |
| Canola* | MPS963 | NA | Phytate breakdown | phyA |

TABLE Z-continued

| Crop | Event Name | Event Code | Trait(s) | Gene(s) |
| --- | --- | --- | --- | --- |
| Canola* | MPS964 | NA | Phytate breakdown | phyA |
| Canola* | MPS965 | NA | Phytate breakdown | phyA |
| Canola* | MS1 (B91-4) | ACS-BNØØ4-7 | Glufosinate tol. | bar |
| Canola* | MS8 | ACS-BNØØ5-8 | Glufosinate tol. | bar |
| Canola* | OXY-235 | ACS-BNØ11-5 | Oxynil tol. | bxn |
| Canola* | PHY14 | NA | Glufosinate tol. | bar |
| Canola* | PHY23 | NA | Glufosinate tol. | bar |
| Canola* | PHY35 | NA | Glufosinate tol. | bar |
| Canola* | PHY36 | NA | Glufosinate tol. | bar |
| Canola* | RF1 (B93-101) | ACS-BNØØ1-4 | Glufosinate tol. | bar |
| Canola* | RF2 (B94-2) | ACS-BNØØ2-5 | Glufosinate tol. | bar |
| Canola* | RF3 | ACS-BNØØ3-6 | Glufosinate tol. | bar |
| Bean | EMBRAPA 5.1 | EMB-PV051-1 | Disease res. | ac 1 (sense and antisense) |
| Brinjal (Eggplant) | EE-1 | | Insect res. | cry1Ac |
| Carnation | 11 (7442) | FLO-07442-4 | SU tol..; modified flower color | surB; dfr; hfl (f3'5'h) |
| Carnation | 11363 (1363A) | FLO-11363-1 | SU tol.; modified flower color | surB; dfr; bp40 (f3'5'h) |
| Carnation | 1226A (11226) | FLO-11226-8 | SU tol.; modified flower color | surB; clfr; bp40 (f3'5'h) |
| Carnation | 123.2.2 (40619) | FLO-4Ø619-7 | SU tol.; modified flower color | surB; dfr; hfl (f3'5'h) |
| Carnation | 123.2.38 (40644) | FLO-4Ø644-4 | SU tol.; modified flower color | surB; dfr; hfl (f3'5'h) |
| Carnation | 123.8.12 | FLO-4Ø689-6 | SU tol.; modified flower color | surB; clfr; bp40 (f3'5'h) |
| Carnation | 123.8.8 (40685) | FLO-4Ø685-1 | SU tol.; modified flower color | surB; dfr; bp40 (f3'5'h) |
| Carnation | 1351A (11351) | FLO-11351-7 | SU tol.; modified flower color | surB; dfr; bp40 (f3'5'h) |
| Carnation | 1400A(11400) | FLO-114ØØ-2 | SU tol.; modified flower color | surB; dfr; bp40 (f3'5'h) |
| Carnation | 15 | FLO-ØØØ15-2 | SU tol.; modified flower color | surB; dfr; hfl (f3'5'h) |
| Carnation | 16 | FLO-ØØØ16-3 | SU tol.; modified flower color | surB; dfr; hfl (f3'5'h) |
| Carnation | 4 | FLO-ØØØ4-9 | SU tol.; modified flower color | surB; dfr; hfl (f3'5'h) |
| Carnation | 66 | FLO-ØØØ66-8 | SU tol.; delayed senescence | surB; acc |
| Carnation | 959A (11959) | FLO-11959-3 | SU tol.; modified flower color | surB; dfr; bp40 (f3'5'h) |
| Carnation | 988A (11988) | FLO-11988-7 | SU tol.; modified flower color | surB; dfr; bp40 (f3'5'h) |
| Carnation | 26407 | IFD-26497-2 | SU tol.; modified flower color | surB; dfr; bp40 (f3'5'h) |
| Carnation | 25958 | IFD-25958-3 | SU tol.; modified flower color | surB; dfr; bp40 (f3'5'h) |
| Chicory | RM3-3 | NA | Glufosinate tol. | bar |
| Chicory | RM3-4 | NA | Glufosinate tol. | bar |
| Chicory | RM3-6 | NA | Glufosinate tol. | bar |
| Cotton | 19-51a | DD-Ø1951A-7 | ALSherbicide tol. | S4-HrA |
| Cotton | 281-24-236 | DAS-24236-5 | Glufosinate tol.; insect res. | pat (syn); cry1F |
| Cotton | 3006-210-23 | DAS-21Ø23-5 | Glufosinate tol.; insect res. | pat (syn); cry1Ac |
| Cotton | 31707 | NA | Oxynil tol.; insect res. | bxn; cry1Ac |
| Cotton | 31803 | NA | Oxynil tol.; insect res. | bxn; cry1Ac |
| Cotton | 31807 | NA | Oxynil tol.; insect res. | bxn; cry1Ac |
| Cotton | 31808 | NA | Oxynil tol.; insect res. | bxn; cry1Ac |
| Cotton | 42317 | NA | Oxynil tol.; insect res. | bxn; cry1Ac |
| Cotton | BNLA-601 | NA | Insect res. | cry1Ac |
| Cotton | BXN10211 | BXN10211-9 | Oxynil tol. | bxn; cry1Ac |
| Cotton | BXN10215 | BXN10215-4 | Oxynil tol. | bxn; cry1Ac |
| Cotton | BXN10222 | BXN10222-2 | Oxynil tol. | bxn; cry1Ac |
| Cotton | BXN10224 | BXN10224-4 | Oxynil tol. | bxn; cry1Ac |
| Cotton | COT102 | SYN-IR102-7 | Insect res. | vip3A(a) |
| Cotton | COT67B | SYN-IR67B-1 | Insect res. | cry1Ab |
| Cotton | COT202 | | Insect res. | vip3A |
| Cotton | Event 1 | NA | Insect res. | cry1Ac |
| Cotton | GMF Cry1A | GTL-GMF311-7 | Insect res. | cry1Ab-Ac |
| Cotton | GHB119 | BCS-GH005-8 | Insect res. | cry2Ae |
| Cotton | GHB614 | BCS-GH002-5 | Glyphosate tol. | 2mepsps |
| Cotton | GK12 | NA | Insect res. | cry1Ab-Ac |
| Cotton | LLCotton25 | ACS-GH001-3 | Glufosinate tol. | bar |
| Cotton | MLS 9124 | NA | Insect res. | cry1C |
| Cotton | MON1076 | MON-89924-2 | Insect res. | cry1Ac |
| Cotton | MON1445 | MON-01445-2 | Glyphosate tol. | cp4 epsps (aroA: CP4) |
| Cotton | MON15985 | MON-15985-7 | Insect res. | cry1Ac; cry2Ab2 |

TABLE Z-continued

| Crop | Event Name | Event Code | Trait(s) | Gene(s) |
|---|---|---|---|---|
| Cotton | MON1698 | MON-89383-1 | Glyphosate tol. | cp4 epsps (aroA: CP4) |
| Cotton | MON531 | MON-00531-6 | Insect res. | cry1Ac |
| Cotton | MON757 | MON-00757-7 | Insect res. | cry1Ac |
| Cotton | MON88913 | MON-88913-8 | Glyphosate tol. | cp4 epsps (aroA: CP4) |
| Cotton | Nqwe Chi 6 Bt | NA | Insect res. | NA? |
| Cotton | SKG321 | NA | Insect res. | cry1A;CpTI |
| Cotton | T303-3 | BCS-GH003-6 | Insect res.; glufosinate tol. | cry1Ab; bar |
| Cotton | T304-40 | BCS-GH004-7 | Insect res.; glufosinate tol. | cry1Ab; bar |
| Cotton | CE43-67B | | Insect res. | cry1Ab |
| Cotton | CE46-02A | | Insect res. | cry1Ab |
| Cotton | CE44-69D | | Insect res. | cry1Ab |
| Cotton | 1143-14A | | Insect res. | cry1Ab |
| Cotton | 1143-51B | | Insect res. | cry1Ab |
| Cotton | T342-142 | | Insect res. | cry1Ab |
| Cotton | PV-GHGTO7 (1445) | | Glyphosate tol. | cp4 epsps (aroA: CP4) |
| Cotton | EE-GH3 | | Glyphosate tol. | mepsps |
| Cotton | EE-GH5 | | Insect res. | cry1Ab |
| Cotton | MON88701 | MON-88701-3 | Dicamba & glufosinate tol. | Modified dmo; bar |
| Cotton | OsCr11 | | Anti-allergy | Modified Cry j |
| Creeping Bentgrass | ASR368 | SMG-368ØØ-2 | Glyphosate tol. | cp4 epsps (aroA: CP4) |
| Eucalyptus | 20-C | | Salt tol. | codA |
| Eucalyptus | 12-5C | | Salt tol. | codA |
| Eucalyptus | 12-5B | | Salt tol. | codA |
| Eucalyptus | 107-1 | | Salt tol. | codA |
| Eucalyptus | Jan. 9, 2001 | | Salt tol. | codA |
| Eucalyptus | Feb. 1, 2001 | | Salt tol. | codA |
| Eucalyptus | | | Cold tol. | des9 |
| Flax | FP967 | CDC-FL001-2 | ALS herbicide tol. | als |
| Lentil | RH44 | | Imidazolinone tol. | als |
| Maize | 3272 | SYN-E3272-5 | Modified alpha-amylase | amy797E |
| Maize | 5307 | SYN-05307-1 | Insect res. | ecry3.1Ab |
| Maize | 59122 | DAS-59122-7 | Insect res.; glufosinate tol. | cry34Ab1; cry35Ab1; pat |
| Maize | 676 | PH-000676-7 | Glufosinate tol.; pollination control | pat; dam |
| Maize | 678 | PH-000678-9 | Glufosinate tol.; pollination control | pat; dam |
| Maize | 680 | PH-000680-2 | Glufosinate tol.; pollination control | pat; dam |
| Maize | 98140 | DP-098140-6 | Glyphosate toll; ALS herbicide tol. | gat4621; zm-hra |
| Maize | Bt10 | NA | Insect res.; glufosinate tol. | cry1Ab; pat |
| Maize | Bt176 (176) | SYN-EV176-9 | Insect res.; glufosinate tol. | cry1Ab; bar |
| Maize | BVLA430101 | NA | Phytate breakdown | phyA2 |
| Maize | CBH-351 | ACS-ZM004-3 | Insect res.; glufosinate tol. | cry9C; bar |
| Maize | DAS40278-9 | DAS40278-9 | 2,4-D tol. | aad-1 |
| Maize | DBT418 | DKB-89614-9 | Insect res.; glufosinate tol. | cry1Ac; pinII; bar |
| Maize | DLL25 (B16) | DKB-89790-5 | Glufosinate tol. | bar |
| Maize | GA21 | MON-00021-9 | Glyphosate tol. | mepsps |
| Maize | GG25 | | Glyphosate tol. | mepsps |
| Maize | GJ11 | | Glyphosate tol. | mepsps |
| Maize | Fl117 | | Glyphosate tol. | mepsps |
| Maize | GAT-ZM1 | | Glufosinate tol. | pat |
| Maize | LY038 | REN-00038-3 | Increased lysine | cordapA |
| Maize | MIR162 | SYN-IR162-4 | Insect res. | vip3Aa20 |
| Maize | MIR604 | SYN-IR604-5 | Insect res. | mcry3A |
| Maize | MON801 (MON80100) | MON801 | Insect res.; glyphosate tol. | cry1Ab; cp4 epsps (aroA: CP4); goxv247 |
| Maize | MON802 | MON-80200-7 | Insect res.; glyphosate tol. | cry1Ab; cp4 epsps (aroA: CP4); goxv247 |
| Maize | MON809 | PH-MON-809-2 | Insect res.; glyphosate tol. | cry1Ab; cp4 epsps (aroA: CP4); goxv247 |
| Maize | MON810 | MON-00810-6 | Insect res.; glyphosate tol. | cry1Ab; cp4 epsps (aroA: CP4); goxv247 |
| Maize | MON832 | NA | Glyphosate tol. | cp4 epsps (aroA: CP4); goxv247 |
| Maize | MON863 | MON-00863-5 | Insect res. | cry3Bb1 |
| Maize | MON87427 | MON-87427-7 | Glyphosate tol. | cp4 epsps (aroA: CP4) |
| Maize | MON87460 | MON-874604 | Drought tol. | cspB |
| Maize | MON88017 | MON-88017-3 | Insect res.; glyphosate tol. | cry3Bb1; cp4 epsps (aroA: CP4) |
| Maize | MON89034 | MON-89034-3 | Insect res. | cry2Ab2; cry1A.105 |
| Maize | MS3 | ACS-ZM001-9 | Glufosinate tol.; pollination control | bar; barnase |
| Maize | MS6 | ACS-ZM005-4 | Glufosinate tol.; pollination control | bar; barnase |

TABLE Z-continued

| Crop | Event Name | Event Code | Trait(s) | Gene(s) |
|---|---|---|---|---|
| Maize | NK603 | MON-00603-6 | Glyphosate tol. | cp4 epsps (aroA: CP4) |
| Maize | T14 | ACS-ZM002-1 | Glufosinate tol. | pat (syn) |
| Maize | T25 | ACS-ZM003-2 | Glufosinate tol. | pat (syn) |
| Maize | TC1507 | DAS-01507-1 | Insect res.; glufosinate tol. | cry1Fa2; pat |
| Maize | TC6275 | DAS-06275-8 | Insect res.; glufosinate tol. | mocry1F; bar |
| Maize | VIP1034 | | Insect res.; glufosinate tol. | vip3A; pat |
| Maize | 43A47 | DP-043A47-3 | Insect res.; glufosinate tol. | cry1F; cry34Ab1; cry35Ab1; pat |
| Maize | 40416 | DP-040416-8 | Insect res.; glufosinate tol. | cry1F; cry34Ab1; cry35Ab1; pat |
| Maize | 32316 | DP-032316-8 | Insect res.; glufosinate tol. | cry 1F; cry34Ab1; cry35Ab1; pat |
| Maize | 4114 | DP4004114-3 | Insect res.; glufosinate tol. | cry1F; cry34Ab1; cry35Ab1; pat |
| Melon | Melon A | NA | Delayed ripening/senescence | sam-k |
| Melon | Melon B | NA | Delayed ripening/senescence | sam-k |
| Papaya | 55-1 | CUH-CP551-8 | Disease res. | prsv cp |
| Papaya | 63-1 | CUH-CP631-7 | Disease res. | prsv cp |
| Papaya | Huanong No. 1 | NA | Disease res. | prsv rep |
| Papaya | X17-2 | UFL-X17CP-6 | Disease res. | prsv cp |
| Petunia | Petunia-CHS | NA | Modified product quality | CHS suppres.sion |
| Plum | C-5 | ARS-PLMC5-6 | Disease res. | ppv cp |
| Canola** | ZSR500 | NA | Glyphosate tol. | cp4 epsps (aroA: CP4); goxv247 |
| Canola** | ZSR502 | NA | Glyphosate tol. | cp4 epsps (aroA: CP4); goxv247 |
| Canola** | ZSR503 | NA | Glyphosate tol. | cp4 epsps (aroA: CP4); goxv247 |
| Poplar | Bt poplar | NA | Insect res. | cry1Ac; API |
| Poplar | Hybrid poplar clone 741 | NA | Insect res. | cry1Ac; API |
| Poplar | trg300-1 | | High cellulose | AaXEG2 |
| Poplar | trg300-2 | | High cellulose | AaXEG2 |
| Potato | 1210 amk | NA | Insect res. | cry3A |
| Potato | 2904/1 kgs | NA | Insect res. | cry3A |
| Canola** | ZSR500 | NA | Glyphosate tol. | cp4 epsps (aroA: CP4); goxv247 |
| Canola** | ZSR502 | NA | Glyphosate tol. | cp4 epsps (aroA: CP4); goxv247 |
| Potato | ATBT04-27 | NMK-89367-8 | Insect res. | cry3A |
| Potato | ATBT04-30 | NMK-89613-2 | Insect res. | cry3A |
| Potato | ATBT04-31 | NMK-89170-9 | Insect res. | cry3A |
| Potato | ATBT04-36 | NMK-89279-1 | Insect res. | cry3A |
| Potato | ATBT04-6 | NMK-89761-6 | Insect res. | cry3A |
| Potato | BT06 | NMK-89812-3 | Insect res. | cry3A |
| Potato | BT10 | NMK-89175-5 | Insect res. | cry3A |
| Potato | BT12 | NMK-89601-8 | Insect res. | cry3A |
| Potato | BT16 | NMK-89167-6 | Insect res. | cry3A |
| Potato | BT17 | NMK-89593-9 | Insect res. | cry3A |
| Potato | BT18 | NMK-89906-7 | Insect res. | cry3A |
| Potato | BT23 | NMK-89675-1 | Insect res. | cry3A |
| Potato | EH92-527-1 | BPS-25271-9 | Modified starch/carbohydrate | gbss (antisense) |
| Potato | HLMT15-15 | NA | Insect & disease res. | cry3A; pvy cp |
| Potato | HLMT15-3 | NA | Insect & disease res. | cry3A; pvy cp |
| Potato | HLMT15-46 | NA | Insect & disease res. | cry3A; pvy cp |
| Potato | RBMT15-101 | NMK-89653-6 | Insect & disease res. | cry3A; pvy cp |
| Potato | RBMT21-129 | NMK-89684-1 | Insect & disease res. | cry3A; plrv orf1; plrv orf2 |
| Potato | RBMT21-152 | NA | Insect & disease res. | cry3A; plrv orf1; plrv orf2 |
| Potato | RBMT21-350 | NMK-89185-6 | Insect & disease res. | cry3A; plrv orf1; plrv orf2 |
| Potato | RBMT22-082 | NMK-89896-6 | Insect & disease res.; Glyphosate tol. | cry3A; plrv orf1; plrv orf2; cp4 epsps (aroA: CP4) |
| Potato | RBMT22-186 | NA | Insect & disease res.; Glyphosate tol. | cry3A; plrv orf1; plrv orf2; cp4 epsps (aroA: CP4) |
| Potato | RBMT22-238 | NA | Insect & disease res.; Glyphosate tol. | cry3A; plrv orf1; plrv orf2; cp4 epsps (aroA: CP4) |
| Potato | RBMT22-262 | NA | Insect & disease res.; Glyphosate tol. | cry3A; plrv orf1; plrv orf2; cp4 epsps (aroA: CP4) |
| Potato | SEMT15-02 | NMK-89935-9 | Insect & disease res. | cry3A; pvy cp |
| Potato | SEMT15-07 | NA | Insect & disease res. | cry3A; pvy cp |
| Potato | SEMT15-15 | NMK-89930-4 | Insect & disease res. | cry3A; pvy cp |

TABLE Z-continued

| Crop | Event Name | Event Code | Trait(s) | Gene(s) |
|---|---|---|---|---|
| Potato | SPBT02-5 | NMK-89576-1 | Insect res. | cry3A |
| Potato | SPBT02-7 | NMK-89724-5 | Insect res. | cry3A |
| Rice | 7Cp#242-95-7 | | Anti-allergy | 7crp |
| Rice | 7Crp#10 | NA | Anti-allergy | 7crp |
| Rice | GM Shanyou 63 | NA | Insect res. | cry1Ab; cry1Ac |
| Rice | Huahui-1/TT51-1 | NA | Insect res. | cry1Ab; cry1Ac |
| Rice | LLRICE06 | ACS-OS001-4 | Glufosinate tol. | bar |
| Rice | LLRICE601 | BCS-OS003-7 | Glufosinate tol. | bar |
| Rice | LLRICE62 | ACS-OS002-5 | Glufosinate tol. | bar |
| Rice | Tarom molaii + cry1Ab | NA | Insect res. | cry1Ab(truncated) |
| Rice | GAT-OS2 | | Glufosinate tol. | bar |
| Rice | GAT-OS3 | | Glufosinate tol. | bar |
| Rice | PE-7 | | Insect res. | Cry1Ac |
| Rice | 7Crp#10 | NA | Anti-allergy | 7crp |
| Rice | KPD627-8 | | High tryptophan | OASA1D |
| Rice | KPD722-4 | | High tryptophan | OASA1D |
| Rice | KA317 | | High tryptophan | OASA1D |
| Rice | HW5 | | High tryptophan | OASA1D |
| Rice | HW1 | | High tryptophan | OASA1D |
| Rice | B-4-1-18 | | Erect leaves semidwarf | Δ OsBRI1 |
| Rice | G-3-3-22 | | Semidwarf | OSGA2ox1 |
| Rice | AD77 | | Disease res. | DEF |
| Rice | AD51 | | Disease res. | DEF |
| Rice | AD48 | | Disease res. | DEF |
| Rice | AD41 | | Disease res. | DEF |
| Rice | 13pNasNaatAprt1 | | Low iron tol. | HvNAS1; HvNAAT-A; APRT |
| Rice | 13pAprt1 | | Low iron tol. | APRT |
| Rice | gHvNAS1-gHvNAAT-1 | | Low iron tol. | HvNAS1; HvNAAT-A; HvNAAT-B |
| Rice | gHvIDS3-1 | | Low iron tol. | HvIDS3 |
| Rice | gHvNAAT1 | | Low iron tol. | HvNAAT-A; HvNAAT-B |
| Rice | gHvNAS1-1 | | Low iron tol. | HvNAS1 |
| Rice | NIA-OS006-4 | | Disease res. | WRKY45 |
| Rice | NIA-OS005-3 | | Disease res. | WRKY45 |
| Rice | NIA-OS004-2 | | Disease res. | WRKY45 |
| Rice | NIA-OS003-1 | | Disease res. | WRKY45 |
| Rice | NIA-OS002-9 | | Disease res. | WRKY45 |
| Rice | NIA-OS001-8 | | Disease res. | WRKY45 |
| Rice | OsCr11 | | Anti-allergy | Modified Cry j |
| Rice | 17053 | | Glyphosate tol. | cp4 epsps (aroA: CP4) |
| Rice | 17314 | | Glyphosate tol. | cp4 epsps (aroA: CP4) |
| Rose | WKS82/130-4-1 | IFD-52401-4 | Modified flower color | 5AT; bp40 (f3'5'h) |
| Rose | WKS92/130-9-1 | IFD-52901-9 | Modified flower color | 5AT; bp40 (f3'5'h) |
| Soybean | 260-05 (G94-1, G94-19, G168) | NA | Modified oil/fatty acid | gm-fad2-1 (silencing locus) |
| Soybean | A2704-12 | ACS-GM005-3 | Glufosinate tol. | pat |
| Soybean | A2704-21 | ACS-GM004-2 | Glufosinate tol. | pat |
| Soybean | A5547-127 | ACS-GM006-4 | Glufosinate tol. | pat |
| Soybean | A5547-35 | ACS-GM008-6 | Glufosinate tol. | pat |
| Soybean | CV127 | BPS-CV127-9 | Imidazolinone tol. | csr1-2 |
| Soybean | DA568416-4 | DA568416-4 | Glufosinate tol. | pat |
| Soybean | DP305423 | DP-305423-1 | Modified oil/fatty acid; ALS herbicide tol. | gm-fad2-1 (silencing locus); gm-hra |
| Soybean | DP356043 | DP-356043-5 | Modified oil/fatty acid; glyphosate tol. | gm-fad2-1 (silencing locus); gat4601 |
| Soybean | FG72 | MST-FG072-3 | Glyphosate & HPPD tol. | 2mepsps; hppdPF W336 |
| Soybean | GTS 40-3-2 (40-3-2) | MON-04032-6 | Glyphosate tol. | cp4 epsps (aroA: CP4) |
| Soybean | GU262 | ACS-GM003-1 | Glufosinate tol. | pat |
| Soybean | MON87701 | MON-87701-2 | Insect res. | cry1Ac |
| Soybean | MON87705 | MON-87705-6 | Modified oil/fatty acid; glyphosate tol. | fatb1-A (sense & antisense); fad2-1A (sense & antisense); cp4 epsps (aroA: CP4) |
| Soybean | MON87708 | MON-87708-9 | Dicamba & glyphosate tol. | dmo; cp4 epsps (aroA: CP4) |
| Soybean | MON87769 | MON-87769-7 | Modified oil/fatty acid; glyphosate tol. | Pj.D6D; Nc.Fad3; cp4 epsps (aroA: CP4) |
| Soybean | MON89788 | MON-89788-1 | Glyphosate tol. | cp4 epsps (aroA: CP4) |
| Soybean | W62 | ACS-GM002-9 | Glufosinate tol. | bar |
| Soybean | W98 | ACS-GM001-8 | Glufosinate tol. | bar |
| Soybean | MON87754 | MON-87754-1 | High oil | dgat2A |

TABLE Z-continued

| Crop | Event Name | Event Code | Trait(s) | Gene(s) |
|---|---|---|---|---|
| Soybean | DAS21606 | DAS-21606 | Aryloxyalkanoate & glufosinate tol. | Modified aad-12; pat |
| Soybean | DAS44406 | DAS-44406-6 | Aryloxyalkanoate, glyphosate & glufosinate tol. | Modified aad-12; 2mepsps; pat |
| Soybean | SYHT04R | SYN-0004R-8 | Mesotrione tol. | Modified avhppd |
| Soybean | 9582.814.19.1 | | Insect res. & glufosinate tol. | cry1Ac, cry1F, PAT |
| Squash | CZW3 | SEM-0CZW3-2 | Disease res. | cmv cp, zymv cp, wmv cp |
| Squash | ZW20 | SEM-0ZW20-7 | Disease res. | zymv cp, wmv cp |
| Sugar Beet | GTSB77 (T9100152) | SY-GTSB77-8 | Glyphosate tol. | cp4 epsps (aroA: CP4); goxv247 |
| Sugar Beet | H7-1 | KM-000H71-4 | Glyphosate tol. | cp4 epsps (aroA: CP4) |
| Sugar Beet | T120-7 | ACS-BV001-3 | Glufosinate tol. | pat |
| Sugar Beet | T227-1 | | Glyphosate tol. | cp4 epsps (aroA: CP4) |
| Sugarcane | NXI-1T | | Drought tol. | EcbetA |
| Sunflower | X81359 | | Imidazolinone tol. | als |
| Sweet Pepper | PK-SP01 | NA | Disease res. | cmv cp |
| Tobacco | C/F/93/08-02 | NA | Oxynil tol. | bxn |
| Tobacco | Vector 21-41 | NA | Reduced nicotine | NtQPT1(antisense) |
| Tomato | 1345-4 | NA | Delayed ripening/senescense | acc (truncated) |
| Tomato | 35-1-N | NA | Delayed ripening/senescense | sam-k |
| Tomato | 5345 | NA | Insect res. | cry1Ac |
| Tomato | 8338 | CGN-89322-3 | Delayed ripening/senescense | accd |
| Tomato | B | SYN-0000B-6 | Delayed ripening/senescense | pg (sense or antisense) |
| Tomato | Da | SYN-0000DA-9 | Delayed ripening/senescense | pg (sense or antisense) |
| Sunflower | X81359 | | Imidazolinone tol. | als |
| Tomato | Da Dong No 9 | NA | Modified product | NA |
| Tomato | F (1401F, h38F, 11013F,7913F) | SYN-0000F-1 | Delayed ripening/senescense | pg (sense or antisense) |
| Tomato | FLAVR SAVR ™ | CGN-89564-2 | Delayed ripening/senescense | pg (sense or antisense) |
| Tomato | Huafan No 1 | NA | Delayed ripening/senescense | anti-efe |
| Tomato | PK-TM8805R (8805R) | NA | Disease res. | cmv cp |
| Wheat | MON71800 | MON-718ØØ-3 | Glyphosate tol. | cp4 epsps (aroA: CP4) |

*Argentine,
**Polish,
Eggplant

Treatment of genetically modified plants and seeds with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants and seeds.

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as Bacillus thuringiensis toxin or those expressing herbicide resistance such as glyphosate acetyltransferase, which provides resistance to glyphosate. Seed treatments with compounds of this invention can also increase vigor of plants growing from the seed.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects,* 1994 BCPC Mongraph No. 57, and references listed therein.

Compounds of Formula 1 and their compositions, both alone and in combination with other insecticides, nematicides, and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides with which compounds of Formula 1 can be formulated to provide mixtures useful in seed treatment include abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of nucleo polyhedrosis viruses.

Fungicides with which compounds of Formula 1 can be formulated to provide mixtures useful in seed treatment include amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtiliis* and *Pasteuria penetrans*. A suitable *Bacillus firmus* strain is strain CNCM I-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by rhizobia bacteria during the initiation of nodule formation on the roots of legumes. For example, the Optimize® brand seed treatment technology incorporates LCO Promoter Technology™ in combination with an inoculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1, an N-oxide, or salt thereof; (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

One embodiment of the present invention relates to a method for controlling invertebrate pests, comprising diluting the pesticidal composition of the present invention (a compound of Formula 1 formulated with surfactants, solid diluents and liquid diluents or a formulated mixture of a compound of Formula 1 and at least one other pesticide) with water, and optionally adding an adjuvant to form a diluted composition, and contacting the invertebrate pest or its environment with an effective amount of said diluted composition.

Although a spray composition formed by diluting with water a sufficient concentration of the present pesticidal composition can provide sufficient efficacy for controlling invertebrate pests, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

Among the spray adjuvants, oils including crop oils, crop oil concentrates, vegetable oil concentrates and methylated seed oil concentrates are most commonly used to improve the efficacy of pesticides, possibly by means of promoting more even and uniform spray deposits. In situations where phytotoxicity potentially caused by oils or other water-immiscible liquids are of concern, spray compositions prepared from the composition of the present invention will generally not contain oil-based spray adjuvants. However, in situations where phytotoxicity caused by oil-based spray adjuvants is commercially insignificant, spray compositions prepared from the composition of the present composition can also contain oil-based spray adjuvants, which can potentially further increase control of invertebrate pests, as well as rainfastness.

Products identified as "crop oil" typically contain 95 to 98% paraffin or naphtha-based petroleum oil and 1 to 2% of one or more surfactants functioning as emulsifiers. Products identified as "crop oil concentrates" typically consist of 80 to 85% of emulsifiable petroleum-based oil and 15 to 20% of nonionic surfactants. Products correctly identified as "vegetable oil concentrates" typically consist of 80 to 85% of vegetable oil (i.e. seed or fruit oil, most commonly from cotton, linseed, soybean or sunflower) and 15 to 20% of nonionic surfactants. Adjuvant performance can be improved by replacing the vegetable oil with methyl esters of fatty acids that are typically derived from vegetable oils. Examples of methylated seed oil concentrates include MSO® Concentrate (UAP-Loveland Products, Inc.) and Premium MSO Methylated Spray Oil (Helena Chemical Company).

The amount of adjuvants added to spray mixtures generally does not exceed about 2.5% by volume, and more typically the amount is from about 0.1 to about 1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Biological Examples of the Invention

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. See Index Tables A-B for compound descriptions.

Formulation and Spray Methodology for Tests A-D

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with ⅛ JJ custom body (Spraying Systems Co. Wheaton, Ill., USA) positioned 1.27 cm (0.5 inches) above the top of each test unit. Test compounds were sprayed at the rates indicated, and each test was replicated three times.

Test A

For evaluating control of green peach aphid (*Myzus persicae* (Sulzer)) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 250 and/or 50 ppm. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality.

Of the compounds of Formula 1 tested at 250 ppm, the following resulted in at least 80% mortality: 3, 10, 11, 12, 14, 15, 20, 22, 23, 30, 52 and 54.

Of the compounds of Formula 1 tested at 50 ppm, the following resulted in at least 80% mortality: 10, 11, 12, 14 and 20.

Test B

For evaluating control of cotton melon aphid (*Aphis gossypii* (Glover)) through contact and/or systemic means, the test unit consisted of a small open container with a 6-7-day-old cotton plant inside. This was pre-infested with 30-40 insects on a piece of leaf according to the cut-leaf method, and the soil of the test unit was covered with a layer of sand.

Test compounds were formulated and sprayed at 250 and/or 50 ppm. After spraying, the test units were maintained in a growth chamber for 6 days at 19° C. and 70% relative humidity. Each test unit was then visually assessed for insect mortality.

Of the compounds of Formula 1 tested at 250 ppm, the following resulted in at least 80% mortality: 15, 22, 23, 36, 42, 46, 47, 48, 51, 54 and 55.

Test C

For evaluating control of the Western Flower Thrips (*Frankliniella occidentalis* (Pergande)) through contact and/or systemic means, the test unit consisted of a small open container with a 5-7-day-old Soleil bean plant inside.

Test compounds were formulated and sprayed at 250 ppm. After spraying, the test units were allowed to dry for 1 hour, and then 22-27 adult thrips were added to each unit. A black, screened cap was placed on top, and the test units were held for 6 days at 25° C. and 45-55% relative humidity.

Of the compounds of Formula 1 tested at 250 ppm, the following provided very good to excellent levels of control efficacy (30% or less plant damage and/or 100% mortality): 10, 11, 12, 13, 15, 16, 17, 19, 20, 22 and 23.

Test D

For evaluating control of the sweetpotato whitefly (*Bemisia tabaci* (Gennadius)) through contact and/or systemic means, the test unit consisted of a small open container with a 12-14-day-old cotton plant inside. Prior to the spray application, both cotyledons were removed from the plant, leaving one true leaf for the assay. Adult whiteflies were allowed to lay eggs on the plant and then were removed from the test unit. Cotton plants infested with at least 15 eggs were submitted to the test for spraying.

Test compounds were formulated and sprayed at 250 and/or 50 ppm. After spraying, the test units were allowed to dry for 1 hour. The cylinders were then removed, and the units were taken to a growth chamber and held for 13 days at 28° C. and 50-70% relative humidity. Each test unit was then visually assessed for insect mortality.

Of the compounds of Formula 1 tested at 250 ppm, the following resulted in at least 50% mortality: 21, 38, 52 and 54.

What is claimed is:
1. A compound selected from Formula 1, an N-oxide or salt thereof,

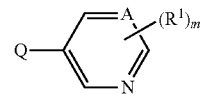

wherein
Q is

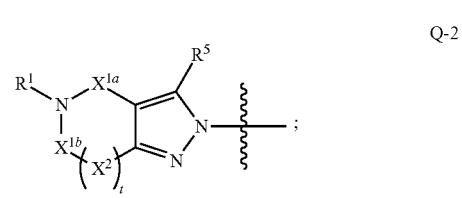

A is CH or N;
$R^1$ is independently halogen, cyano, nitro, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio or $C_1$-$C_4$ haloalkylthio; m is 0;
$X^{1a}$ is $CH_2$;
$X^{1b}$ is $CH_2$;
$X^2$ is $CH_2$;
t is 1;
$R^2$ is $C(=O)R^4$ or $C(=O)NR^6R^7$;
$R^4$ is H; or $C_1$-$C_6$ alkyl, $C_3$-$C_6$ cycloalkyl, $C_2$-$C_6$ alkenyl, $C_2$-$C_6$ alkynyl, $C_1$-$C_6$ alkoxy, $C_1$-$C_6$ haloalkoxy or $C_3$-$C_6$ cycloalkoxy, each unsubstituted or substituted with at least one $R^x$; or $C(O)OR^{21}$, $C(O)NR^{15}R^{16}$ or $C(O)R^{22}$;
$R^5$ is H;
$R^6$ is H, $NR^{15}R^{16}$, $OR^{17}$, $C(=NR^{10})R^{11}$, $C(O)OR^{21}$, $C(O)NR^{15}R^{16}$, $C(O)R^{22}$, $S(O)_nR^{23}$ or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$;
$R^7$ is H or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one $R^x$; or
$R^6$ and $R^7$ are taken together with the nitrogen atom to which they are attached to form a 3- to 10-membered ring containing ring members selected from carbon atoms and up to 2 heteroatoms independently selected from one oxygen atom, one sulfur atom, and up to 2 nitrogen atoms, wherein up to 2 carbon atom ring members are independently selected from $C(=O)$ and $C(=S)$ and the sulfur atom ring member is selected from S, $S(O)$ or $S(O)_2$, said ring being unsubstituted or substituted with up to 4 $R^x$; or
$R^6$ and $R^7$ are taken together as $=S(O)_pR^{18}R^{19}$ or $=S(=NR^{20})R^{18}R^{19}$;
each $R^x$ is independently halogen, cyano, nitro, hydroxy, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_3$-$C_6$ cycloalkoxy, $C(=NR^{10})R^{11}$, $C(O)OR^{21}$, $C(O)NR^{15}R^{16}$, $OC(O)R^{22}$, $NR^{25}R^{26}$, $NR^{24}C(O)R^{22}$, $C(O)R^{22}$, $S(O)_nR^{23}$, $Si(R^{28})_3$, $OSi(R^{28})_3$ or $Q^a$;
each $R^y$ is independently halogen, cyano, hydroxy, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_3$-$C_6$ cycloalkoxy, C(=NR$^{10}$)R$^{11}$, C(O)OR$^{21}$, OC(O)R$^{22}$, NR$^{25}$R$^{26}$, NR$^{24}$C(O)R$^{22}$, C(O)R$^{22}$ or Q$^a$;
each R$^{10}$ is independently OR$^{12}$, S(O)$_n$R$^{13}$ or NHR$^{14}$;
each R$^{11}$ is independently H; or C$_1$-C$_6$ alkyl, C$_3$-C$_6$ cycloalkyl, C$_2$-C$_6$ alkenyl or C$_2$-C$_6$ alkynyl, each unsubstituted or substituted with at least one R$^x$; or C$_1$-C$_6$ alkoxy, C$_1$-C$_6$ haloalkoxy, C$_3$-C$_6$ cycloalkoxy, C(O)OR$^{21}$, C(O)NR$^{15}$R$^{16}$, C(O)R$^{22}$;
each R$^{12}$ is independently C$_1$-C$_4$ alkyl, C$_3$-C$_6$ cycloalkyl, C$_1$-C$_4$ haloalkyl, C(O)R$^{22}$, S(O)$_n$R$^{13}$ or Q$^a$;
each R$^{13}$ is independently C$_1$-C$_4$ alkyl or C$_1$-C$_4$ haloalkyl;
R$^{14}$ is C$_1$-C$_4$ alkyl, C$_3$-C$_6$ cycloalkyl, C$_1$-C$_4$ haloalkyl, C(O)R$^{22}$ or C(O)OR$^{21}$; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
R$^{15}$ is H, NR$^{15a}$R$^{16a}$, OR$^{17}$, C(=NR$^{10}$)R$^{11}$, C(O)OR$^{21}$, C(O)NR$^{15a}$R$^{16a}$, C(O)R$^{22}$ or S(O)$_n$R$^{23}$; or C$_1$-C$_6$ alkyl, C$_3$-C$_6$ cycloalkyl, C$_2$-C$_6$ alkenyl or C$_2$-C$_6$ alkynyl, each unsubstituted or substituted with at least one R$^x$;
R$^{16}$ is H; or C$_1$-C$_6$ alkyl, C$_3$-C$_6$ cycloalkyl, C$_2$-C$_6$ alkenyl or C$_2$-C$_6$ alkynyl, each unsubstituted or substituted with at least one R$^x$; or
R$^{15}$ and R$^{16}$ are taken together with the nitrogen atom to which they are attached to form a 3- to 10-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with up to 4 R$^x$; or
R$^{15}$ and R$^{16}$ are taken together as =S(O)$_p$R$^{18}$R$^{19}$ or =S(=NR$^{20}$)R$^{18}$R$^{19}$;
each R$^{15a}$ is independently H, C$_1$-C$_6$ alkyl, C$_1$-C$_4$ haloalkyl, C(O)R$^{27}$ or S(O)$_2$R$^{27}$; or phenyl or a 5- or 6-membered heterocyclic aromatic ring, each unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{16a}$ is independently H, C$_1$-C$_6$ alkyl or C$_1$-C$_4$ haloalkyl; or
R$^{15a}$ and R$^{16a}$ are taken together with the nitrogen atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
R$^{17}$ is C$_1$-C$_4$ alkyl, C$_3$-C$_6$ cycloalkyl or C$_1$-C$_4$ haloalkyl; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{18}$ is independently C$_1$-C$_4$ alkyl or C$_1$-C$_4$ haloalkyl; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{19}$ is independently C$_1$-C$_4$ alkyl or C$_1$-C$_4$ haloalkyl; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy; or
R$^{18}$ and R$^{19}$ are taken together with the sulfur atom to which they are attached to form a ring;
R$^{20}$ is H, cyano, C$_1$-C$_4$ alkyl, C$_1$-C$_4$ haloalkyl or C(O)R$^{22}$; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{21}$ is independently C$_1$-C$_4$ alkyl, C$_1$-C$_4$ haloalkyl, C$_3$-C$_6$ cycloalkyl or C$_3$-C$_6$ halocycloalkyl; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{22}$ is independently C$_1$-C$_4$ alkyl, C$_1$-C$_4$ haloalkyl, C$_3$-C$_6$ cycloalkyl, C$_3$-C$_6$ halocycloalkyl, C$_1$-C$_6$ alkoxy, C$_1$-C$_6$ haloalkoxy, C$_3$-C$_6$ cycloalkoxy or NR$^{25}$R$^{26}$; or
phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{23}$ is independently C$_1$-C$_4$ alkyl, C$_1$-C$_4$ haloalkyl, C$_3$-C$_6$ cycloalkyl, C$_3$-C$_6$ halocycloalkyl, C$_3$-C$_6$ cycloalkylalkyl or C$_3$-C$_6$ halocycloalkylalkyl; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{24}$ is independently C$_1$-C$_4$ alkyl;
each R$^{25}$ is independently H, C$_1$-C$_4$ alkyl, C$_1$-C$_4$ haloalkyl, C$_1$-C$_4$ alkoxy or C$_1$-C$_4$ haloalkoxy; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy;
each R$^{26}$ is independently C$_1$-C$_4$ alkyl or C$_1$-C$_4$ haloalkyl; or phenyl, unsubstituted or substituted with at least one substituent independently selected from the group consisting of halogen, cyano, nitro, C$_1$-C$_4$ alkyl, C$_3$-C$_6$ cycloalkyl, C$_1$-C$_4$ haloalkyl, C$_1$-C$_4$ alkoxy and C$_1$-C$_4$ haloalkoxy; or
R$^{25}$ and R$^{26}$ are independently taken together with the nitrogen atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{27}$ is independently $C_1$-$C_6$ alkyl, $C_1$-$C_6$ haloalkyl, $C_1$-$C_6$ alkoxy, $C_1$-$C_6$ haloalkoxy or $NR^{29}R^{30}$; or phenyl or a 5- or 6-membered heterocyclic aromatic ring, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{28}$ is independently $C_1$-$C_6$ alkyl, $C_3$-$C_6$ cycloalkyl or phenyl;

each $R^{29}$ is independently H or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $R^{30}$ is independently H or $Q^a$; or $C_1$-$C_6$ alkyl, $C_3$-$C_6$ cycloalkyl, $C_2$-$C_6$ alkenyl or $C_2$-$C_6$ alkynyl, each unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy; or $R^{29}$ and $R^{30}$ are taken together with the nitrogen atom to which they are attached to form a 3- to 10-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with up to 4 substituents independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each $Q^a$ is independently phenyl, a 5- or 6-membered heterocyclic aromatic ring or a 3- to 6-membered heterocyclic non-aromatic ring, each ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, each ring unsubstituted or substituted with at least one substituent independently selected from the group consisting of halogen, cyano, nitro, $C_1$-$C_4$ alkyl, $C_3$-$C_6$ cycloalkyl, $C_1$-$C_4$ haloalkyl, $C_1$-$C_4$ alkoxy and $C_1$-$C_4$ haloalkoxy;

each n is independently 0, 1 or 2; and p is 1 or 2.

2. A composition comprising a compound of claim 1 and at least one additional component selected from the group consisting of surfactants, solid diluents and liquid diluents, said composition optionally further comprising at least one additional biologically active compound or agent.

3. The composition of claim 2 wherein the at least one additional biologically active compound or agent is selected from the group consisting of abamectin, acephate, acequinocyl, acetamiprid, acrinathrin, afidopyropen, amidoflumet, amitraz, avermectin, azadirachtin, azinphos-methyl, benfuracarb, bensultap, bifenthrin, bifenazate, bistrifluron, borate, buprofezin, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyclaniliprole, cycloprothrin, cycloxaprid, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin, flonicamid, flubendiamide, flucythrinate, flufenerim, flufenoxuron, flufenoxystrobin, flufensulfone, fluorpyram, flupiprole, flupyradifurone, fluvalinate, tau-fluvalinate, fonophos, formetanate, fosthiazate, halofenozide, heptafluthrin, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiodicarb, methomyl, methoprene, methoxychlor, metofluthrin, monocrotophos, monofluthrin, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide, pymetrozine, pyrafluprole, pyrethrin, pyridaben, pyridalyl, pyrifluquinazon, pyriminostrobin, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tolfenpyrad, tralomethrin, triazamate, trichlorfon, triflumuron, all strains of *Bacillus thuringiensis*, entomopathogenic bacteria, all strains of *Nucleo polyhedrosis* viruses, entomopathogenic viruses and entomopathogenic fungi.

4. The composition of claim 3 wherein the at least one additional biologically active compound or agent is selected from the group consisting of abamectin, acetamiprid, acrinathrin, afidopyropen, amitraz, avermectin, azadirachtin, benfuracarb, bensultap, bifenthrin, buprofezin, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, lambda-cyhalothrin, gamma-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, fluvalinate, formetanate, fosthiazate, heptafluthrin, hexaflumuron, hydramethylnon, imidacloprid, indoxacarb, lufenuron, meperfluthirn, metaflumizone, methiodicarb, methomyl, methoprene, methoxyfenozide, metofluthrin, monofluthrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, tetramethylfluthrin, triazamate, triflumuron, all strains of *Bacillus thuringiensis* and all strains of *Nucleo polyhedrosis* viruses.

5. A method for controlling an invertebrate pest comprising contacting the invertebrate pest, its environment, a plant, or seed from which the plant is grown with a biologically effective amount of a compound of claim 1.

6. The method of claim 5 wherein the seed is coated with the compound of claim 1 formulated as a composition comprising a film former or adhesive agent.

7. A treated seed comprising a compound of claim 1 in an amount of from about 0.0001 to 1% by weight of the seed before treatment.

* * * * *